(12) United States Patent
Reese et al.

(10) Patent No.: US 8,839,796 B2
(45) Date of Patent: Sep. 23, 2014

(54) APPARATUS AND SYSTEM FOR AUGMENTED DETAINEE RESTRAINT

(75) Inventors: Corbin Reese, Scottsdale, AZ (US);
Donald L. Pegg, Chandler, AZ (US);
Lucius L. Lockwood, Phoenix, AZ (US)

(73) Assignee: Scottsdale Innovations, LLC, Paradise Valley, AZ (US)

( * ) Notice: Subject to any disclaimer, the term of this patent is extended or adjusted under 35 U.S.C. 154(b) by 211 days.

(21) Appl. No.: 13/508,031

(22) PCT Filed: Oct. 29, 2010

(86) PCT No.: PCT/US2010/054825
§ 371 (c)(1),
(2), (4) Date: Aug. 20, 2012

(87) PCT Pub. No.: WO2011/056732
PCT Pub. Date: May 12, 2011

(65) Prior Publication Data
US 2012/0298119 A1    Nov. 29, 2012

Related U.S. Application Data

(60) Provisional application No. 61/258,129, filed on Nov. 4, 2009, provisional application No. 61/292,605, filed on Jan. 6, 2010.

(51) Int. Cl.
*A61F 5/37*    (2006.01)

(52) U.S. Cl.
USPC ............................................. 128/875; 70/16

(58) Field of Classification Search
USPC ............... 128/869, 874–875; 602/16, 20, 23; 70/16
See application file for complete search history.

(56) References Cited

U.S. PATENT DOCUMENTS

| | | | | |
|---|---|---|---|---|
| 4,089,195 A | * | 5/1978 | Lai | 70/16 |
| 4,370,696 A | * | 1/1983 | Darrell | 361/232 |
| 4,811,775 A | * | 3/1989 | Sun | 361/232 |
| 5,841,622 A | * | 11/1998 | McNulty, Jr. | 361/232 |

* cited by examiner

*Primary Examiner* — Michael A. Brown
(74) *Attorney, Agent, or Firm* — Snell & Wilmer LLP

(57) ABSTRACT

There is provided a device and system for restraining detainees through devices attached to the detainees and configured to administer electrical shocks when certain predetermined conditions occur. Restraining devices may be activated by internal control systems or by external controllers that transmit activation signals to the restraining device. External controllers may be actuated by an external controlling entity such as a detention guard or other person or system, or may be controlled by an enabling signal sent by wired or wireless connections to the controller. There is also provided a system for detainee restraint where multiple detainees may be restrained collectively or individually in a controlled environment such as a detention facility, a jail, or a detainee transport vehicle.

15 Claims, 24 Drawing Sheets

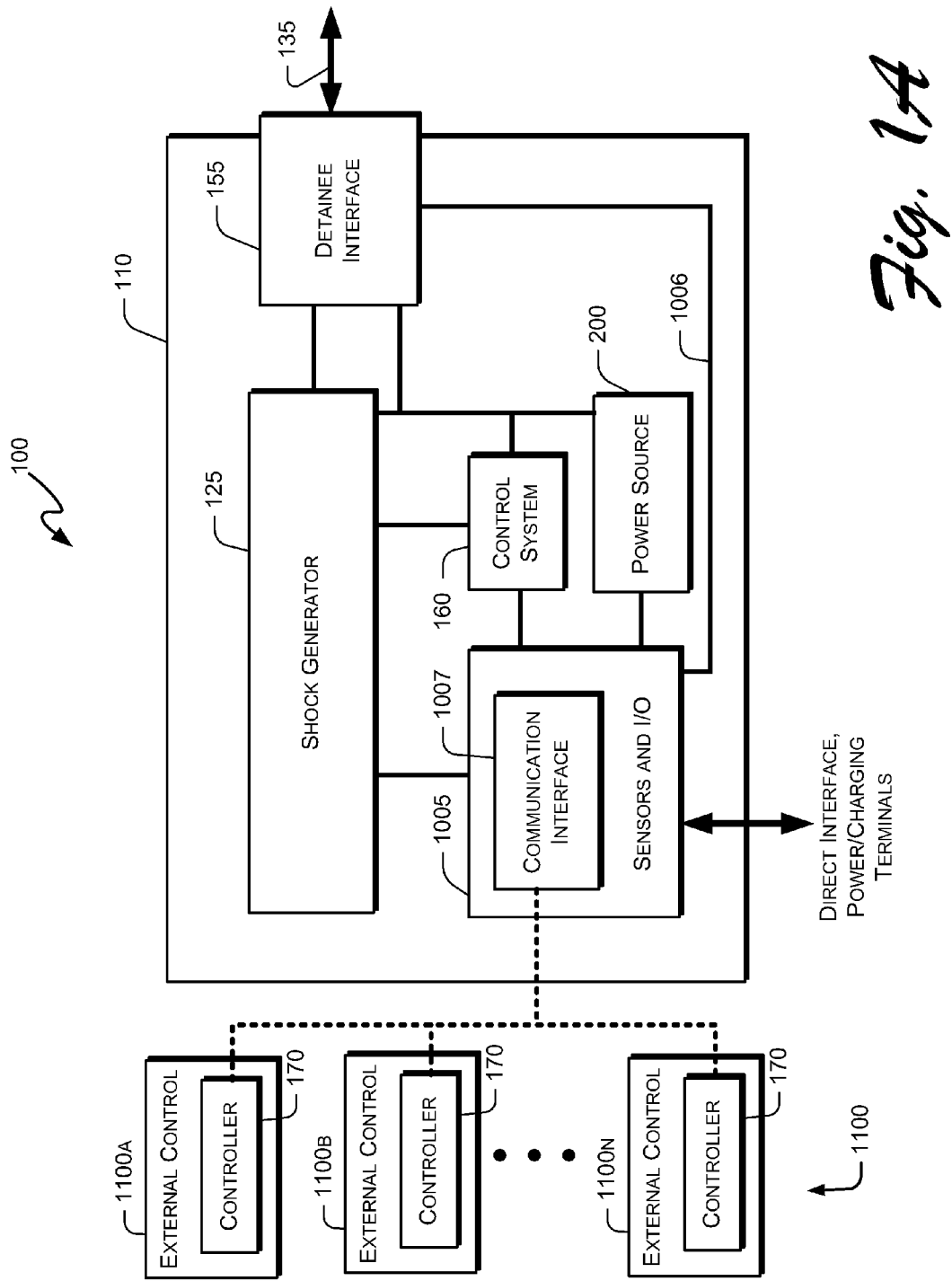

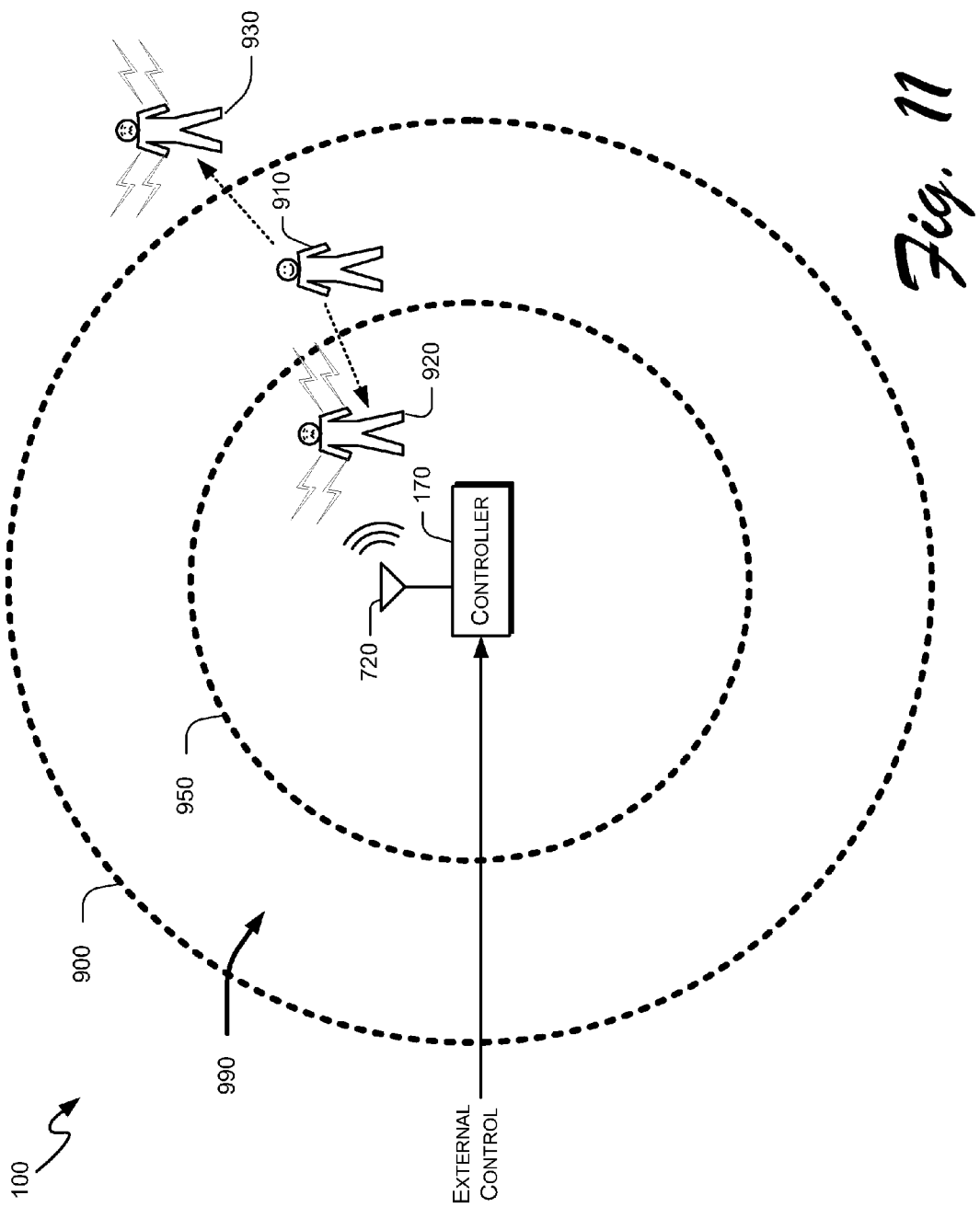

ined to make contact. One must wind up in succession. They are generally more cumbersome than Taser-

APPARATUS AND SYSTEM FOR AUGMENTED DETAINEE RESTRAINT

CROSS REFERENCE TO RELATED APPLICATIONS

This application claims priority to U.S. Provisional Patent Application No. 61/258,129 filed on Nov. 4, 2009 and U.S. Provisional Patent Application No. 61/292,605 filed on Jan. 6, 2010, the respective disclosures of which are incorporated by reference in their entirety.

FIELD OF THE INVENTION

The present invention relates to systems, devices, and methods utilizing restraints and electric shock devices to restrain detainees, and more particularly to at least one restraint cuff with an integrated electrical shock mechanism.

BACKGROUND OF THE INVENTION

Stun guns are sold commercially for use in law enforcement, security applications, and self-defense. The principal behind stun gun application is basic. The body's electrical system is an efficient communication system where the brain instructs designated nerve cells to release a neurotransmitter, which is a communication chemical to muscle cells. At any given time, thousands of neurotransmitter signals are being sent throughout the body, and stun guns may disrupt this communication system. Stun guns generate a high-voltage, low-amperage electrical current. In simple terms, this means that the current has a significant pressure behind it, but not much intensity. When a stun gun is pressed against an attacker and the trigger is pressed, a charge passes into the attacker's body. Since it has a fairly high voltage the current will pass through heavy clothing and skin. At around 3 milliamps, the current is not intense enough to damage the attacker's body unless it is applied for extended periods of time. However, the delivered current results in a confusing amount of information on the attacker's nervous system. First the current combines with the electrical signals from the attacker's brain. Any original signal is mixed with what appears to be random noise, making it very difficult to decipher any messages. When these lines of communication are overwhelmed, the attacker has a very hard time instructing his muscles to move, and he may become confused and unbalanced.

The current may be generated with a pulse frequency that mimics the body's own electrical signals. In this case, the current will tell the attacker's muscles to do a great deal of work in a short amount of time. Since the work performed by the attacker's muscles during shock depletes the attacker's energy reserves, the attacker ideally becomes too weak to move.

There are varying models and techniques of stun weapons in use today. The three most popular devices, the handheld stun gun, the Taser type gun, and the liquid stun gun.

Stun-gun effectiveness varies depending on the particular gun model, the attacker's body size and his determination. Another factor is how long the gun is maintained in contact with the attacker and correspondingly, the length of time when shock is administered. If the gun is actuated for half a second, a painful jolt may startle the attacker. If the gun is applied and shock administered for one or two seconds, the attacker should experience muscle spasms and become dazed. If the attacker receives more than three seconds of shock, he will likely become unbalanced and disoriented and may lose muscle control. However, determined attackers with a certain physiology may keep coming despite any shock.

Conventional stun guns have a fairly simple design. They are about the size of a flashlight, and they work on ordinary batteries. The battery supplies electricity to a circuit consisting of various electrical components. The circuitry includes multiple transformers, components that boost the voltage in the circuit, typically to between 20,000 and 150,000 volts, and reduce the amperage. Conventional stun guns also include an oscillator, a component that fluctuates current to produce a specific pulse pattern of electricity. This current charges a capacitor. The capacitor builds up a charge, and releases it to the electrodes, the portion of the circuit where the shocking current is delivered to the attacker. The electrodes are often two plates of conducting metal positioned in the circuit with a gap between them. Since the electrodes are positioned along the circuit, they have a high voltage difference between them. If this gap is filled with a conductor (say, the attacker's body), the electrical pulses will try to move from one electrode the other, dumping electricity into the attacker's nervous system.

One popular variation on the conventional stun-gun design is the Taser-type gun. Taser-type guns work the same basic way as ordinary stun guns, except the two charge electrodes aren't permanently joined to the housing. Instead, they are positioned at the ends of long conductive wires, attached to the gun's electrical circuit. Pulling the trigger breaks open a compressed gas cartridge inside the gun. The expanding gas builds pressure behind the electrodes, launching them through the air, the attached wires trailing behind. The electrodes are affixed with small barbs so that they will grab onto an attacker's clothing or skin. When the electrodes are attached, the current travels down the wires into the attacker, providing a stunning effect in a similar manner as a conventional stun gun.

The main advantage of the Taser-type design is that attackers can be stunned from a greater distance (typically 15 to 20 feet/4 to 6 meters). One disadvantage is that the person using the gun only gets one shot to make contact. One must wind up and re-pack the electrode wires, as well as load a new gas cartridge, each time the device is fired. Most models also have conventional stun-gun electrodes, in case the flying electrodes miss the target.

One of the newer stun weapons is the liquid stun gun. These devices work the in a similar manner to Taser-type guns except they use a liquid stream to conduct electricity rather than extended wires. The liquid stun gun is connected to a tank of highly conductive liquid, typically a mixture of water, salt and various other conductive elements. When the trigger is pulled, electrical current travels from the gun, through the liquid stream, to the attacker. These guns have a longer firing range than Taser-type guns, and can be shot many times in succession. They are generally more cumbersome than Taser-type guns, however, because of the need to store, transport, and emit conductive liquid. High-powered guns work with vehicle-mounted water cannons, while portable models typically include a water tank backpack.

Most current stun-gun models have two pairs of electrodes: an inner pair and an outer pair. The outer pair of electrodes is spaced a distance apart, so current will only flow if an outside conductor, such as an attacker's body part, is inserted. If the current cannot flow across these electrodes, it flows to the inner pair of test electrodes. These electrodes are close enough that the electric current can leap between them through an air gap. The moving current ionizes the air particles in the gap, producing a visible spark and crackling noise. This display is mainly intended as a deterrent. An attacker sees and hears the electricity and knows that the person holding the stun gun is capable of administering a shock. Some stun guns rely on the element of surprise, rather than producing a warning. These models are disguised as umbrellas, flashlights or other everyday objects that may catch attackers off guard.

Handcuffs are more traditionally used by law enforcement, and security forces. Handcuffs are restraining devices designed to secure an individual's wrists close together. They comprise two halves, linked together by a chain, hinge or in the case of rigid cuffs, a bar. Each half has a rotating part which engages with a ratchet which is closed around a person's wrist. Without the key, the person cannot move their wrists more than a few centimeters/inches apart, making many tasks difficult or impossible. This is usually done to prevent suspected criminals from escaping police custody. There are two distinct subtypes of contemporary metal handcuffs: one in which the cuffs are held together by a short chain, and another, of more recent origin, which uses a hinge for this purpose. Since the hinged handcuffs are somewhat smaller when fully extended they are seen as being more easily utilized by a police officer who has relatively small hands, and are also regarded by some observers as more secure because the wrists end up being held closer together than with the chain subtype, and are also bound more rigidly. A third type, the rigid handcuff, has a metal block or bar between the cuffs. While bulkier to carry, it permits several variations in cuffing. An example of rigid handcuffs is Hiatts Speedcuffs as used by most police forces in the United Kingdom. Both rigid and hinged cuffs can be used one-handed to apply pain-compliance/control techniques that are not workable with the chain type of cuff. Various accessories are available to improve the security or increase the rigidity of handcuffs, including boxes that fit over the chain or hinge and can themselves be locked with a padlock.

Handcuffs with double locks have a lock-spring that when engaged stops the cuff from ratcheting tighter to prevent the wearer from tightening them. Tightening could be intentional or by struggling, when tightened the handcuffs may cause nerve damage or loss of circulation. Also, some wearers could tighten the cuffs to attempt an escape by having the officer loosen the cuffs and while the cuffs are loose attempt the escape. Double locks also make picking the locks more difficult.

Three kinds of double locks for handcuffs include the lever lock, the push pin lock, and the slot lock. The lever lock is double-locked by fully lifting the lever with a fingertip and then allowing it to return. This causes the lock spring to move into a position that locks the bolt thus preventing the cuff from being further tightened. Thus no tool is required to double lock of this kind. The push pin lock is double-locked by fully depressing the push pin using the small peg on the top of the key. This causes the lock spring to move into a position that locks the bolt thus preventing the cuff from being further tightened. The slot lock is double-locked by inserting the small peg on the top of the key into the double lock slot. In this position, the small peg can contact the end of the lock spring. The key is then slid towards the key hole. This causes the lock spring to move into a position that locks the bolt, thus preventing the cuff from being further tightened.

On occasions when a suspect exhibits extremely aggressive behavior, leg irons may be used as well; sometimes the chain connecting the leg irons to one another is looped around the chain of the handcuffs, and then the leg irons are applied, resulting in the person being "hog-tied". In a few rare cases, hog-tied persons lying on their stomachs have died from positional asphyxia, making the practice highly controversial, and leading to its being severely restricted, or even completely banned, in many localities. However, when a person is restrained within handcuffs and/or leg irons there are many reports of these individuals escaping and/or causing serious injuries to law enforcement personnel. Thus, a need exists for a device, which overcomes these and other restraint and separate electric shock device problems.

SUMMARY OF THE INVENTION

There is provided a device and system for restraining detainees through devices attached to the detainees and configured to administer electrical shocks when certain predetermined conditions occur. Restraining devices may be activated by internal control systems or by external controllers that transmit activation signals to the restraining device. External controllers may be actuated by an external controlling entity such as a detention guard or other person or system, or may be controlled by an enabling signal sent by wired or wireless connections to the controller. There is also provided a system for detainee restraint where multiple detainees may be restrained collectively or individually in a controlled environment such as a detention facility, a jail, or a detainee transport vehicle.

Embodiments of the restraining device of the present invention includes a restraint for physically constraining movement of at least a portion of a detainee's body; an electric shock component coupled to the restraint; and a control system coupled to the electric shock component, the control system configured to cause the electric shock component to deliver a shock to the detainee when a predetermined condition occurs. The restraining device may be any device capable of being attached to a detainee and restraining at least a portion of the detainee's body, and in various implementations may include at least one of: a handcuff; an ankle cuff; a restraining belt; a straightjacket; a harness; a facial restraint; a helmet; and a neck collar; and combinations thereof. The restraint further includes one or more electrodes coupled to the electric shock component, and one of the one or more electrodes are configured to contact the skin of the detainee to deliver a shock when a predetermined condition occurs. Warnings in various forms may be provided to the detainee by the restraining device prior to administration of shock, and may be managed selectively by the control system coupled to the restraining device. Examples of warnings may include one or more of: an audio warning; a tactile warning such as a vibration or low-intensity shock; a visual warning such as a flashing light or text indicating a shock may be administered; and combinations thereof. The warnings may be varied in intensity to attempt to modify behavior of the detainee prior to administration of a shock, and the output of the administered shock may be tailored to a predetermined or variable amount based upon conditions perceived by an external controlling entity.

In various embodiments, the shock output of the restraining device may be varied to achieve any desired result. For example, the control system may be configured to cause the electric shock component to vary at least one of: a magnitude of the electric shock; a frequency of a signal generating the electric shock; and duration of the electric shock.

Embodiments of the restraining device may further include one or more sensors in communication with the control system. A sensor may be configured to detect whether the detainee engages in an unauthorized activity, and when such condition occurs the control system may be configured to deliver a shock to the detainee. The unauthorized activity may be defined to include any condition such as the detainee entering an unauthorized location; the detainee approaching a restricted area within a predetermined distance; the detainee approaching a keep-out zone broadcasting a keep-out signal, wherein a signal power level of the keep-out signal received by the device exceeds a predetermined threshold; the detainee attempting to tamper with the restraining device; or the detainee exiting an authorized location. Additionally, unauthorized activities may include the detainee making a threatening movement, where the restraining device measures through its sensors that the detainee is making movements of an aggressive nature or is modifying posture to a posture of potential aggression, such as drawing back a fist to swing, raising an arm suddenly, yanking against the restraining device, or rising suddenly from a prone or seated posture. Also, sensors on the restraining device may determine an unauthorized activity has occurred when the detainee makes an utterance that exceeds a predetermined volume measured by sensors coupled to the restraining device (such as a microphone); such a situation may be desirable to prevent the detainee from interfering in court proceedings, for example. In another embodiment, an unauthorized activity may include use of an unauthorized system such as any structure, device, or system to which use or access by the detainee can be controlled, including: a door to a building, ignition to a police car, computer system, or a weapon. In one embodiment, if a weapon is equipped with an RFID or other identification device, sensors in the restraining device may transmit a signal and receive a response signal indicating that a weapon is in a predetermined the proximity, and if the detainee does not move away from the weapon to cause the response signal to fall below a predetermined threshold, a shock will be administered. In yet another embodiment, an unauthorized activity occurs when the detainee fails to provide a predetermined verbal acknowledgement. Various combinations of these states may lead to additional unauthorized activities being detected.

The restraining device may be configured to measure any desired parameter, and in various embodiments, a sensor coupled to the restraining is configured to measure and store one or more of: a status of the electric shock component; a status of the restraint; a status of the detainee; and a record of shocks administered to the detainee. The record of shocks administered may contain any desired information such as time and date of shock administration; severity of shock delivered; reason the shock was administered; identifying information of a controller or controlling entity instructing the restraining device to administer the shock, etc. Sensors coupled to the restraining device may include any type of sensor to achieve any desired result. For example, sensors may include one or more of an accelerometer; an inclinometer; a potentiometer; a location sensing device; a microphone; a camera; a biometric sensor; and combinations thereof.

The control system of the restraining device of claim may operate the device in any desired manner, and in one embodiment is configured to communicate with one or more controlling entities remote to the device. Controlling entities may include any person, system, or device capable of sending information to, and/or receiving information from the device, including a human (by visual, audial, or tactile means), or other device or system (e.g. electronically or by automated control). Such communications may include at least one of: a wireless data transmission; a transmission of an analog audio signal; a transmission of a signal digitally encoding at least one of audio information and data; a signal encoded with information comprising a command to be interpreted by the control system; a signal encoded with authentication information; and a signal comprising status information regarding the device. In various embodiments, the communication between the control system and the one or more external entities includes one or more of: a command provided by the external entity to the control system, the command for controlling one or more functions of the device; a status provided by the control system to the external entity, the status relating to at least one of: data relating to the detainee; and one or more components of the device; a message provided by the external entity to the control system, the message for delivery to the detainee through one or more output devices in communication with the control system; information provided by the control system to the external entity, the information collected by one or more sensors in communication with the control system; and various combinations thereof. Those of skill in the relevant arts also appreciate that secure control can be achieved by encryption of communications between the restraining device and one or more external controlling entities and/or controllers.

Various embodiments of the restraining device of the present invention also comprise a substance delivery system in communication with the control system, wherein the control system is configured to cause the substance delivery system to expose the detainee to the substance. The substance may includes any substance capable of being stored or delivered by the restraining device to achieve any desired result, and may be a least one of a liquid, a gas, a dye, an irritant, a medication, a sedative, a transdermal medication or transdermal enhancers such as dimethyl sulfoxide, a chemical restraint, a paralytic, a medication prescribed to the detainee, and combinations thereof. In some embodiments, the restraining device may be configured to inject the substance through a movable needle or gas injection system. Administration of such substances may be in addition to or in place of any electric shocks delivered by the restraining device, and substances may be delivered to achieve any desired goal such as providing a needed medication to a patient; preventing occurrence of uncontrollable psychotic episodes or seizures, suppression of undesirable behavior, chemical restraint when electrical restraint is insufficient (such as in the case if a energy storage device in the restraining device has insufficient charge state) or any other desired reason.

Another embodiment includes a method for restraining a detainee with a provided movement-limiting restraining device including a selective current delivery component, the method comprising: attaching the provided restraining device to at least a portion of the detainee's body; activating the restraining device to transition the current delivery component from a quiescent mode to an active mode; detecting a predetermined condition has occurred indicating that an electric shock component coupled to the restraining device is to be activated; and delivering an electric shock to the detainee.

The predetermined condition may include any desired criteria, and may be selected from the group consisting of: the detainee approaching a restricted area within a predetermined distance; the detainee approaching a keep-out zone broadcasting a keep-out signal, wherein a signal power level of the keep-out signal received by the restraining device exceeds a predetermined threshold; the detainee exiting from an authorized location; the detainee making a threatening movement; the detainee annunciating an utterance that exceeds a predetermined volume; the detainee attempting to tamper with the device; the detainee using an unauthorized system; the detainee failing to provide a predetermined verbal acknowledgement; and combinations thereof.

Embodiments also include transmitting an activation signal from a controller to the restraining device, wherein the activation signal received by the restraining device indicates that the predetermined condition has occurred. The controller may transmit an activation signal (or conversely a deactivation signal) upon occurrence of any desired condition. For example, the controller may transmit an activation signal when a controlling entity actuates a switch coupled to the controller, such as when a detention officer presses a button on the controller. The controller may also itself be controlled by an external controlling entity. Aspects of the present invention include transmitting an enabling signal to the controller, wherein the enabling signal received by the controller causes the controller to transmit the activation signal to the restraining device. The enabling signal may be transmitted with a predetermined power level to limit activation of the restraining device to a predetermined area, and may be continually transmitted by the controller, such as in the case where an exit is to be protected from detainee's approach, or a detention officer wearing a low-power controller broadcasting an enabling signal so that detainees may not approach the officer too closely (or within a predetermined distance). Additionally, aspects include transmitting a disabling signal to the controller, wherein the disabling signal received by the controller prevents the controller to from transmitting the activation signal to the restraining device.

Another embodiment of the present invention includes transmitting an enabling signal to the controller, wherein the enabling signal received by the controller causes the controller to transmit the activation signal to the restraining device. Further aspects also allow for transmitting a keep-in activation signal from a controller to the restraining device; and determining that the predetermined condition has occurred when a power level of the keep-in signal received by the restraining device falls below a predetermined threshold.

Data may be obtained from sensors coupled to the restraining device and may be stored or transmitted to an external controller. The data may comprise any desired information, such as information regarding administration of electrical shocks to the detainee. The external controller or control system coupled to the restraining device may act upon the information, for instance, suppressing the transmission of an activation signal from the controller to the restraining device when the information regarding administration of electrical shocks to the detainee satisfies a predetermined condition. For example, the predetermined condition may comprise determining that a number of electrical shocks administered within a predetermined time period exceeds a predetermined shock administration frequency.

In one embodiment the electric shock mechanism includes one or more electrodes situated within a handcuff-like restraint that deliver an electric shock. These electrodes are positioned so that the electrodes touch the skin when the cuffs are positioned on a person. The physical portion of the restraint can have an inside surface that touches the skin of a detainee when in use and the one or more electrodes are positioned on the inside surface of at least one of the restraint. One restraining device may be attached to a detainee and then attached to an object to at least partially restrain movement of a detainee's body part, for example, a wrist cuff may be attached to a table, a wall, a cable, or the like, and may operate to deliver a shock when certain conditions are satisfied. Alternatively, as described in more detail below, two or more restraints may be used together in a manner similar to conventional handcuffs. In some embodiments where two devices are utilized in handcuff configuration, each of the cuffs has an inside surface and one or more electrodes is positioned on each inside surface. In another embodiment the device includes four cuffs.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1A illustrates a block diagram depiction of a system embodiment of the present invention using restraining devices of the present invention interfaced to external controlling entities.

FIG. 11 shows a system of the present invention implementing a safe zone through a combination of keep-in and keep out boundaries boundary for detainee restraint.

DETAILED DESCRIPTION OF PREFERRED EMBODIMENTS

Reference will now be made in detail to the present exemplary embodiments of the invention, examples of which are illustrated in the accompanying drawings.

Restraining Device 110 and System 110

Figure 1B:
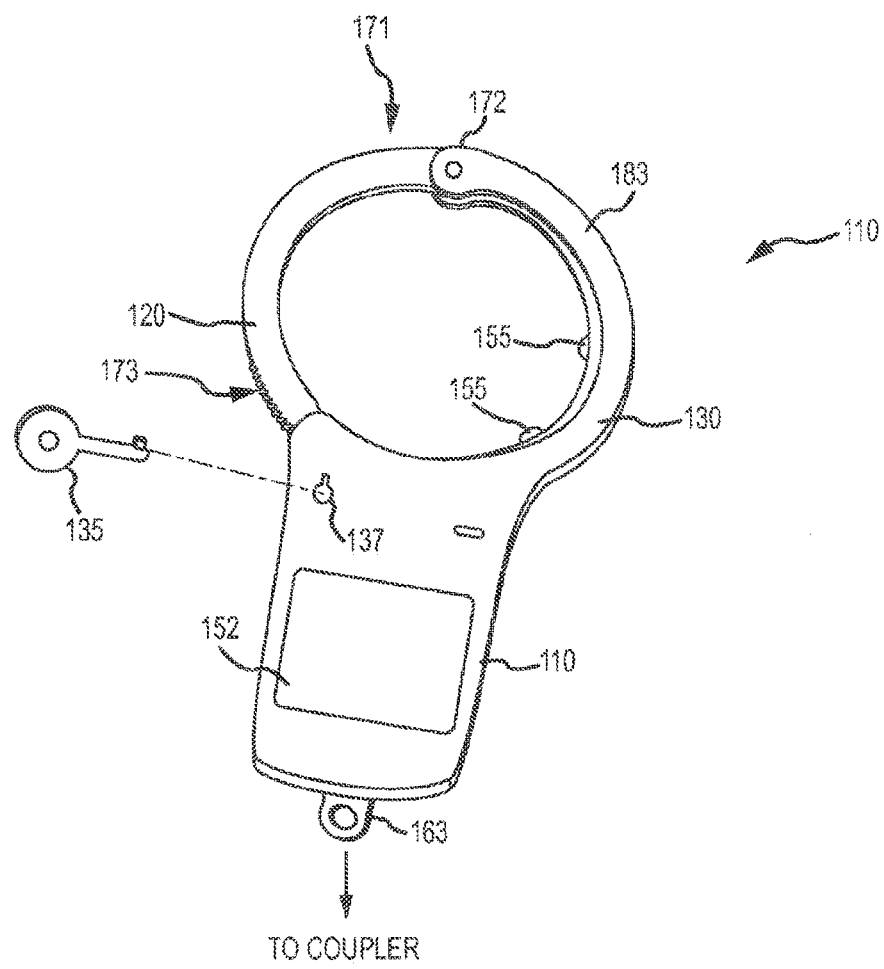
FIG. 1B shows one embodiment of a restraining device of the present invention.

A block diagram depiction of a system 100 using restraining devices 110 interfaced to external controlling entities 1100 is shown in FIG. 1A. A generalized embodiment of a restraining device 110 comprises a shock generator component 150 coupled to a control system 160; sensors and I/O with communications interface 1005; a power source 200; and a detainee interface 155 that comprises a current delivery interface such as electrodes. As discussed in more detail below, the shock generator component 150 is configured, upon receiving a control system from the control system 160, to present one or more high voltage, low current pulses to the detainee interface, which may comprise conductive electrodes, conductive strips, an air gap, or any interface suitable to deliver electric current to the skin of a detainee. In a preferred embodiment, the detainee interface comprises metallic electrodes coupled to a housing that also includes the restraining device 110. Embodiments of housings are discussed in more detail below.

In one embodiment power source 200 provides an energy source for the electric shock component 150, and all other electronic components within the restraining device 110. For instance, power source 200 may operate sensors 1005 including a communication interface 1007 comprising a wired terminal connection and/or a receiver/transceiver and antenna; a geolocation/Global Positioning System or "GPS" circuit; locking and unlocking mechanism; control system 160, alarm and/or status indicators. As used herein, the terms "GPS" and "geolocation" may be used interchangeably. The power source 200 is capable of energizing the electric shock component 150 to supply a scalable nonlethal electric shock. Redundant and/or secondary power sources may be implemented as a backup to the primary power source 200 or to power secondary systems such as sensors or locking and unlocking mechanisms. These redundant power sources may provide the same or different output voltage than the power source 200.

Power source 200 may comprise any structure, device or component capable of powering device components such as a capacitor, battery, inductor, transformer, AC source and/or a combination thereof. The power source 200 may be charged by receiving a charging current through external connection points coupled to the restraining device 110 or through a wireless charging interface wherein a transformer inductively couples a charging current to the power source 200. The power source may comprise any suitable battery type such as an alkaline battery, lithium battery, lithium-ion battery, lithium ion polymer battery, nickel-cadmium battery, nickel-iron battery, nickel hydrogen battery, nickel metal hydride battery, nickel-zinc battery, rechargeable alkaline battery, but are preferably lithium iron phosphate (LiFePO$_4$) batteries. Embodiments utilizing a capacitor may comprise any suitable capacitor such as supercapacitors, ultra capacitors, Mylar, ceramic, mica, glass, plastic, and/or paper but in the preferred embodiment are ceramic.

Control system 160

The control system 160 directs the operation of the restraining device 110. The control system 160 may interface with and control any of the individual components of the restraining system 100, such as the electric shock component 150, power source 200, sensors and communication interface 1007, locking and unlocking mechanism (discussed below), as well as any other systems and devices internal and/or external to the system such one or more external controlling entities 1100 using a remote controller 170. Any process implemented and/or controlled by the control system 160 may be operated manually, such as by a human operator or other control system, and/or configured to operate automatically, such as under the control of a software program.

The control system 160 may control any function and aspect of the system 100 to achieve any desired result. The control system 160 may schedule, direct, and manage communications and resources for the system. In some embodiments, the control system 160 may be implemented as a processor coupled to a memory; various systems and processes may be controlled by one or more software programs stored the memory of the control system operating on one or more processors in the control system. In alternate embodiments, the control system 160 may comprise hard wired digital logic and/or circuitry to implement control of the restraining device 110. The control system 160 can function as a stand-alone controller to cause a shock to be delivered, for instance, when a predetermined condition is measured by the sensors 1005 coupled to the control system 160, or may be directed by another system or device, such as a remote controller 170. The control system 160 may be coupled to the electric shock component 150 through any suitable means such as wired, through hole wire leads, wirelessly, and/or by printed circuit board but in the preferred embodiment the control system 160 is coupled to the electric shock component 150 and other system components by a printed circuit board. If desired, wire leads may be coupled between the printed circuit board and the detainee interface 155. For example, the control system 160 may control the operation of the discharging and/or recharging of the power source 200 through external charging terminals or inductively coupled charging interface. Alternatively, the control system 160 may control the scaling of the electric output level and/or duration of electric shock. The control system 160 is electrically coupled to and controls the operation of sensors 1005 of the restraining device 110 which may include any appropriate sensors such as clocks, light sensors, voltage sensors, charge status monitors, motion sensors, potentiometers, status indicators, accelerometers, strain or pressure sensors, inclinometers, location sensing devices such as a GPS devices, audio sensors/microphones, cameras, magnetic field sensors; moisture sensors; EKG/ECG sensors; biometric sensors and combinations thereof. Also, sensors may be included that measure time, intensity and duration of the discharge of the system, number of uses remaining may be provided. Input/Output aspects of the restraining device 110 are also provided for by sensors and I/O 1005, and in various embodiments, may include keys, buttons, keyboards, electrical terminals or connectors, electrical charging ports, data ports such as a USB port, touch screens, displays, speakers, transducers, vibratory agitators, light emitting diodes, strobe lights, infrared light emitting diodes and the like.

As sensors 1005 are coupled 1006 to the detainee interface 155 and/or electric shock component 150, sensors may measure, process and/or store aspects of application of electric shocks to the detainee to whom the restraining device 110 is attached. The control system 160 may cause sensors to measure, store, and/or transmit through the communication interface 1007 or I/O 1005 the measured time, intensity and duration of electric shocks provided to the detainee interface; a number of uses remaining from a charge status of the power source 200; location, such as a GPS coordinate where a shock was administered; a recording of audio or video information from the restraining device 110; or actions taken by the detainee prior to administration of a shock such as a sudden detected motion or attempt to remove or disable the restraining device 110.

The sensors 1005 may work in concert with the control system 160 and/or controller 170 to produce a desired result. For instance, if the GPS circuit senses a current location of restraining device 110 is not within a preselected area or predetermined distance from a predetermined location, control system 160 may activate the unit to provide a warning and/or electric shock automatically. Alternatively, a controller 170 operator may program a predetermined "home" GPS coordinate and the control system 160 will measure if a location of a restraining device 110 affixed to a detainee is not within a preset distance from the home coordinate. If the detainee to whom the restraining device 110 is affixed moves beyond the preset distance a warning and/or an electric shock may be delivered to the detainee. The restraining device 110 sensors 1005, such as the GPS sensor, may be continuously activated or activated by the operator of the controller 170 or the control system 160. In an alternate implementation, the GPS may provide measurements allowing the controller 160 of the restraining device 110 to determine that the detainee to whom the restraining device 110 is affixed moves closer than a minimum distance to a predetermined location or a plurality of predetermined locations that may constitute a threshold boundary. If a current distance of the detainee to whom the restraining device 110 is affixed is less than the threshold boundary distance, a warning and/or an electric shock may be delivered to the detainee. A historical record or real time status of a restraining device's GPS locations may be tracked and stored in a memory of the control system 160, and may be accessed through a port connected to I/O 1005, or may be transmitted from the communication interface 1007 to an external controlling entity 1100 utilizing a controller 170 (described below).

The sensors may work in concert with the control system 160 and/or controller 170 (described below) to produce a desired result. For instance, if a geolocation sensor in the restraining device 110 (such as a GPS circuit) senses the restraining device 110 location is not within a preselected boundary or distance from a predetermined location, control system 160 may activate the unit to provide a warning and/or electric shock automatically. Alternatively, an external controlling entity 1100 may transmit to the communication interface 1007 of the restraining device 110 a predetermined GPS coordinate and the control system 160 will measure if the detainee and/or the restraining device 110 exceed a preset distance from the fixed GPS coordinate. If the detainee and/or restraining device 110 exceed the preset distance a warning and/or an electric shock shall be delivered to the detainee. The restraining device 110 sensors, such as the GPS sensor, may be continuously activated or activated by the operator of the controller 170 or the control system 160. Or, the GPS may measure that a detainee and/or restraining device 110 moves closer than a minimum distance to a fixed location or a plurality of fixed locations that may constitute a boundary. If the distance of the detainee and/or restraining device 110 is less than the preset distance a warning and/or an electric shock shall be delivered to the detainee. A historical record or real time status of a detainee's or multiple restraining device detainees GPS locations may be generated for review on a hand held controller 170 and/or on a computer base station controller 170.

A timer may measure when the restraining device 110 was activated, such as when the devices issued a warning and/or electric shock, or when the device was unlocked or locked. A motion sensor may record when a detainee is brought to the ground during restraining device 110 activation. Alternatively, a motion sensor may indicate that a detainee who has left a predefined boundary or distance from a predetermined location is stationary or moving. An audio sensor such as a microphone, speaker, and provided software, may permit two-way communication between a detainee of restraining device 110 and a controller 170 operator. Additionally, a speaker may provide a siren indicating that a detainee has left a predetermined boundary or distance from a predetermined location assisting in detainee retrieval and notification to others. In an alternative embodiment a light source may provide a visual indicator, such as a strobe, that a detainee has left a predetermined boundary or distance from a predetermined location assisting in detainee retrieval and notification to others. A magnetic field sensor may enable the use of specialized keys for unlocking the mechanism. A status indicator may provide an indication that the restraining device 110 is in a closed position and/or armed, with remaining battery life and electric shock pulses available.

Additionally, an audio sensor and video sensor may be activated on the unit to permit communications with the detainee and an external entity 1100 using a controller 170. In some embodiments, a speaker may be included in the restraining device 110 to present the detainee with an audible warning that an electric shock will be initiated based on predetermined conditions continuing and/or occurring. The audible warning may comprise a tone, sound, or spoken instructions. Alternatively, an agitation module may be located on restraining device 110 to vibrate the restraining device 110 and present the detainee with a vibration warning that an electric shock is imminent and/or will be initiated based on predetermined condition continuing and/or occurring. In some embodiments, a light source may be included on the restraining device 110 to present the detainee with a visual warning, such as a flashing light, that an electric shock is imminent and/or will be initiated based on predetermined conditions continuing and/or occurring. The predetermined conditions may include the detainee moving closer to a predetermined boundary or location, the detainee continuing or initiating unacceptable behavior, at least a portion of the detainee's body being placed in a threatening position, activation of a strain or pressure sensor in the restraining device 110 indicating the detainee is pulling against the attached restraining device 110; and/or the operator of the controller desiring to deliver an electric shock to the detainee.

External controlling entities 1100 comprise one or more persons, automated systems, or facilities capable of controlling the restraining device 110 through use of remote controller 170. The controlling entities 1100 may include law enforcement officers, prison guards, detention officers, or other personnel operating one or more mobile controllers 170, or a may also comprise remote monitoring system that may send an activation signal to the communication interface 1007 of the restraining device. The transmission of information between the controlling entities 1100 and the restraining device 110 may be one way, or may provide two-way communications wherein status information, audio and/or video data, and other data may be relayed from the restraining device to the external controlling entities. In an embodiment, each restraining device 110 in the system 110 possesses a unique identifier to allow tracking, monitoring, and control of individual restraining devices among a plurality of such devices.

Figure 2:
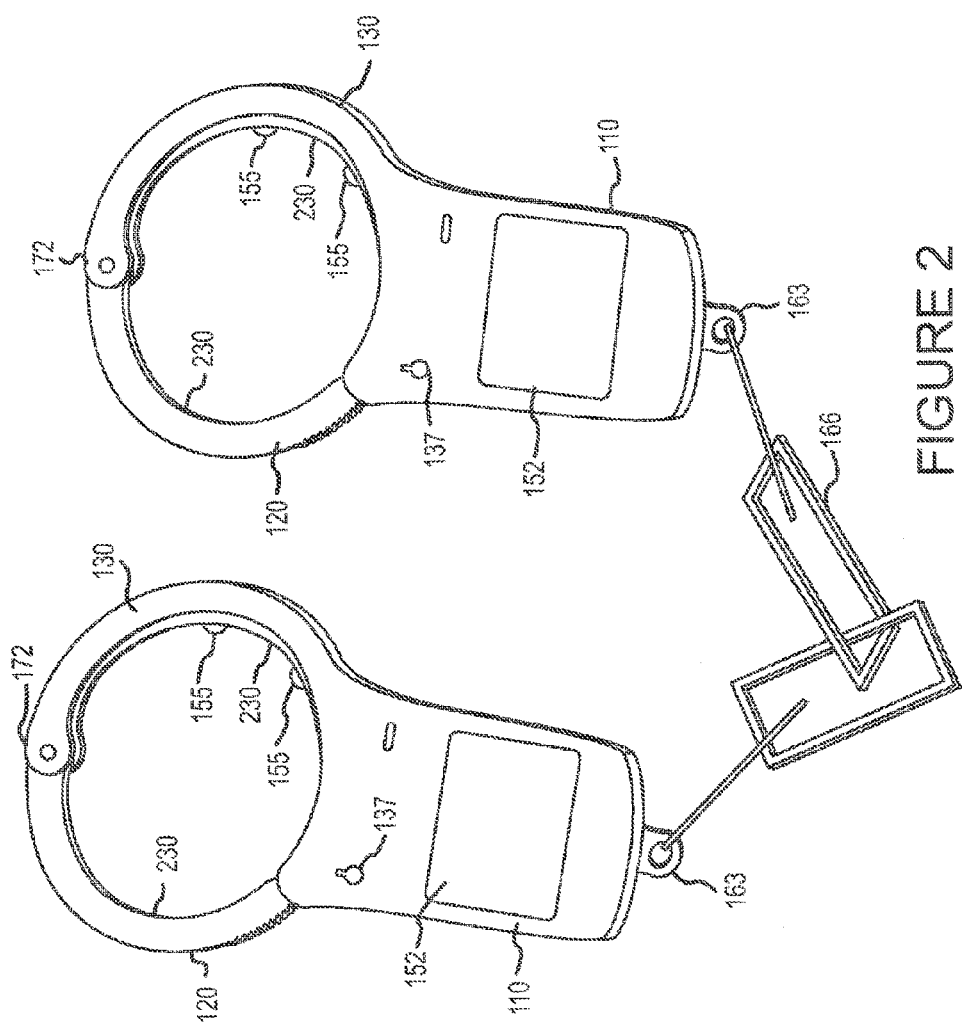
FIG. 2 depicts a pair of interconnected restraining devices shown in FIG. 1A.

In various embodiments, the restraining device 110, as seen in FIGS. 1B and 2-4, is configured to both constrain movement of at least a portion of a detainee's body and deliver an electric shock to the detainee when predetermined conditions occur. In some implementations, restraining device 110 comprises a restraining member 120, a receiving member 130, a coupling point 163, a power source 140 and an electric shock component 150 disposed at least partially within a housing 152 in the restraining device 110. In an embodiment, the housing is substantially water- and tamper-resistant, and is configured to prevent detainee access and/or detect unauthorized access, entry, or attempts to disable the electric shock component. In some embodiments restraining device 110 optionally comprises a control system 160, controller 170, and a comfort material such as deformable or compressible polymer. Restraining device 110 may be any suitable size, with any suitable width, opening size, weight, color and/or shape. Restraining device 110 may be made from any suitable material and/or materials such as various metals, carbon steel, stainless steel, copper, titanium, or aluminum, various metal alloys, carbon fiber, graphite, and/or synthetic polymers. In some embodiments, as seen in FIG. 2, the coupling points 163 of a plurality of restraining devices 110 may be coupled together through a flexible restraining link 166 such as chain, metal links, cable, or cord, and may be attached to a detainee's wrists, ankles, or other body parts to at least partially constrain motion. In other embodiments a single restraining device 110 is coupled to an additional restraint, such as restraining device 110 attached to a detainee's torso, and then coupled to a standard set of restraints, such as handcuffs commonly used by law enforcement. In another embodiment, restraining device 110 is coupled from its coupling point 163 through a flexible or rigid coupling tether such as cable, chain, link, hinge, rod, or carabineer to an object such as a table, a wall, a chair, a vehicle, or any other device that may constrain freedom of movement of the detainee. The coupling tether may be any length or gauge but is preferably a short length of chain so that detainee's range of motion is restricted. In one embodiment the coupling point 163 is forged, welded, molded, or otherwise connected to the restraining device 110 so as to provide sufficient mechanical strength to prevent a typical detainee from escaping detainment by pulling or yanking against the attached and coupled restraining device. Add-ons, such as chain lock boxes, or padlocks for use with hinges may be added to the restraining device 110.

In some embodiments, insulation is attached to or molded on the outer surface of restraining device 110. The insulation may provide weather proofing, protection from the transfer of electrical shock and/or aid in comfort for the detainee. Additionally, in other embodiments, fur, feathers, leather, faux materials, sequins and/or other eye pleasing coatings or coverings may be added to the exterior of restraining device 110. Restraining device 110 may be transported when not in use in any suitable manner such as clipped to clothing, stored in a utility belt, disposed in a holster and/or carried by a strap, but in the preferred embodiment restraining device 110 is transported when not in use in a holster.

Similarly to embodiments shown in FIG. 1A., in various configurations, restraining devices of the present invention such as the illustrated restraining device 110 may also comprise one or more of a speaker, microphone, charging ports, strain or pressure sensor, biometric sensor, EKG sensor, data ports, status indicators, such as battery level, locked or unlocked status, antenna, audio sensor, video sensor, an agitator for producing vibration, power source, electric shock component, memory, and/or control system (all described below).

Restraining Member 120 and Receiving Member 130

In one embodiment restraining device 110 comprises a restraining member 120 that works in concert with a receiving member 130 that attaches to at least a portion of a detainee. The portion of the detainee may comprise any body part such as one or more of a wrist, arm, head, leg, finger, ankle, neck, toe, genitals, torso and/or waist. In the preferred embodiment, the restraining device 110 is coupled to one or more of the detainee's wrists, and in another preferred embodiment, two restraining devices 110 that are coupled together through a flexible tether are attached to a detainee's wrists.

In one embodiment, as shown in FIGS. 1-2, the restraining device includes a rigid receiving member 130 and a restraining member 120. In one embodiment, an arcuate restraining member is hingably coupled at a hinge point 172 to rigid receiving member 130 while a clasping end 173 of the restraining member 120 is receivably inserted into an aperture in the receiving member 130. The outer distal surface of the clasping end 173 of the restraining member 120 may have jagged protrusions that engage a ratchet like assembly within the receiving member 130, thereby securing the restraining member from opening at various positions based on a positioning of the protrusion and protrusion catch within the receiving member 130. In an embodiment, the clasping end of the restraining member 120 may be inserted into the aperture with application of force but may not be removed and/or dislodged without the use of a tool 135 and/or code, further described below. A double lock such as a lever lock, a push-pin lock, or slot lock may be implemented to secure the restraining device 110 in a closed (locked) secure position.

In one embodiment, the receiving member 130 includes protruding electrodes (further described below) configured to receive a restraining member 120 and secure a portion of the detainee's body. Receiving member 130 comprises a housing portion 152 for housing a power supply, electric shock component and sensors, and a coupling arm 183 for coupling to the restraining member 120. The coupling arm to the restraining member may be any shape but, as shown in FIG. 1, is preferably arcuate or "C"-shaped so that both the "C" shaped opening of the restraining member 120 and the "C" shaped coupling arm 183 of the receiving member 130 face each other. The housing portion 152 of the receiving member 130 may be any size suitable for securely housing at least the power supply 200 and electric shock component 150. As shown in FIGS. 1 and 2, the front face of this portion 152 is substantially rectangular shaped. The housing portion of receiving member 130 may be any thickness for suitably securely restraining device 110 elements but in the present embodiment it is between about 0.5 and about 2 centimeters thick. Receiving member 130, like restraining member 120, may be made out of any suitable material such as various metals, including carbon steel, stainless steel and aluminum, metal alloys, carbon fiber, graphite, and/or from synthetic polymers. In the preferred embodiment the receiving member 130 comprises stainless steel.

The restraining member 120 and receiving member 130 comprise at least a first open position where a detainee may insert a portion of a body part such as a wrist, between the restraining member 120 and a receiving member 130 when in their hingedly open position. In one embodiment the restraining member 120 and receiving member 130 are designed to at least partially circumferentially surround the provided portion of the detainee's body when in a closed position. The restraining member 120 is then moved from a first open position into a closed position where the clasping end 172 of the restraining member 120 is coupled to the receiving member 130 whereby the detainee cannot remove an inserted body portion until restraining device 110 is returned to a first open position.

The positioning of the closed position of restraining device 110 may be scalable to accommodate a variety of sizes of body parts. For instance, an obese adult male detainee's wrist may be significantly larger than the wrist of a slender female detainee, so the locked position of the restraining device 110 accommodates a variety of part sizes when in the closed and locked position. Also, the size of restraining device 110 is scalable and may be designed to enclose any desired body part. The size of restraining device 110 and the opening created by the receiving member 120 designed for use on a detainee's thumb may be different from the size of restraining device 110 designed for a detainee's wrist.

The restraining device 110 may be made out of any suitable material such as fabric, metal, synthetics, plastic and/or combinations thereof. However, in the preferred embodiment the frame of restraining device 110 is made out of stainless steel. The width of the restraining member 120 is any suitable width and may vary with material. For instance, a metal restraining member 120 may be between about 0.25 and about 3 centimeters in width. Also, the thickness of the restraining member 120 may be any suitable dimension and may vary with material. For instance, a metal restraining member 120 may be about 1 centimeter thick.

Figure 3:
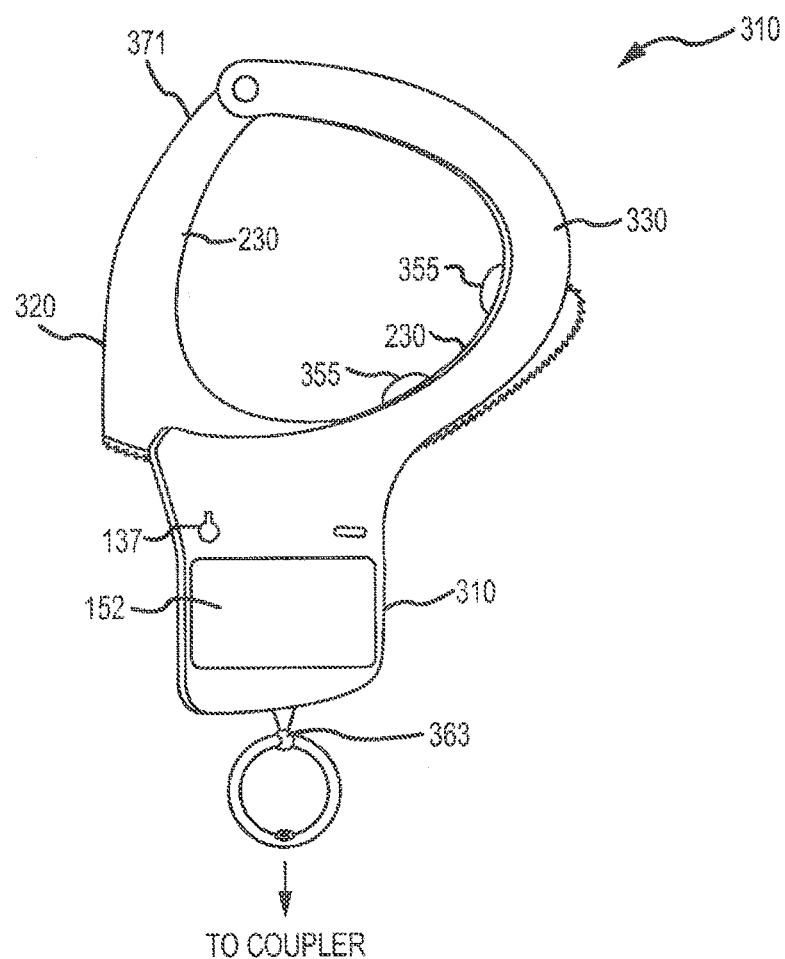
FIG. 3 depicts another embodiment of the restraining device in accordance with systems and methods consistent with the present invention.

An alternate embodiment of restraining device 310 is depicted in FIG. 3. This device 310 would be suitable for use on various portions of a detainee's body but is preferably implemented on a detainee's ankle. Restraining device 310 comprises an "L" shaped restraining member 320 pivotally coupled to a distal end 371 of a receiving member 330, at least one electrode 355 for providing a nonlethal electric shock (preferably two) and a coupling point for coupling to other restraining devices and or other restraints. Restraining device 310 functions similarly to restraining device 110 described above.

Figure 4A:
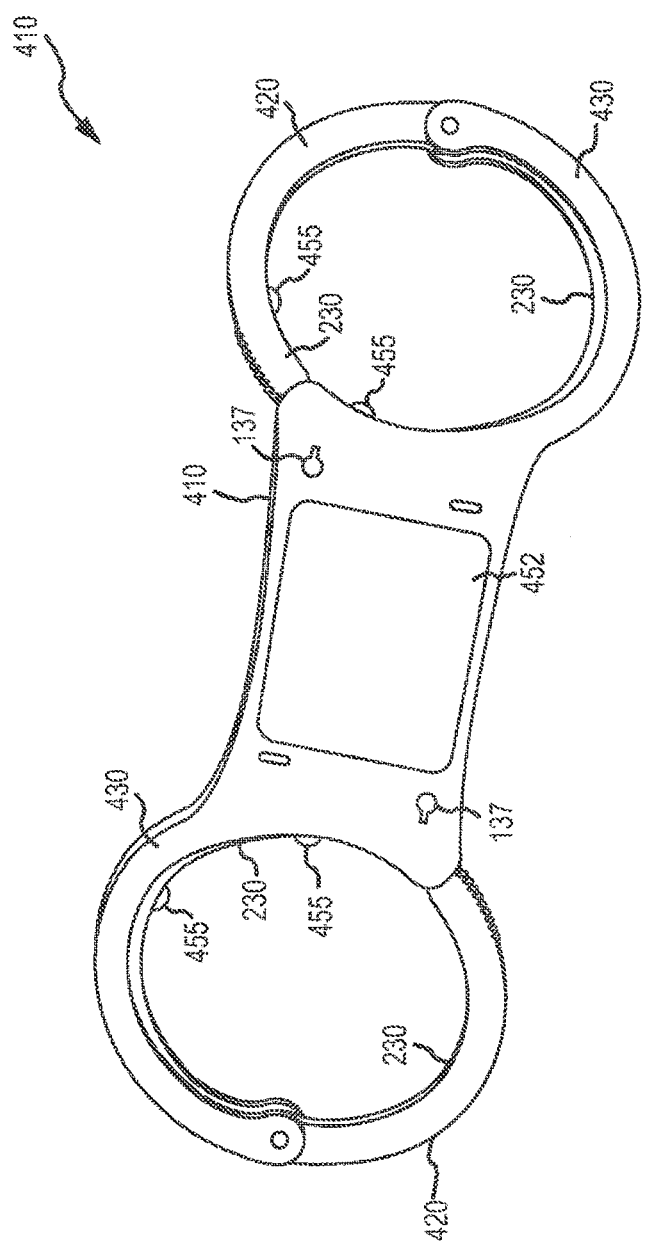
FIG. 4A depicts yet another embodiment of the restraining device in accordance with systems and methods consistent with the present invention.

As seen in FIG. 4A, in some embodiments the restraining device 410 will have two restraining members 420 coupled to a central receiving member 430. This central receiving member 430 may have one or two power supplies for providing an electric shock (as described below). This central receiving member 430 may also have one or two electric shock components (as described below) disposed within a central housing portion 452, and any suitable number of electrodes 455, but preferably two sets of electrodes 455 (four total). Restraining device 410 may be used on various portions of the body but is preferably configured for use on for use on a detainee's wrists.

Figure 4B:
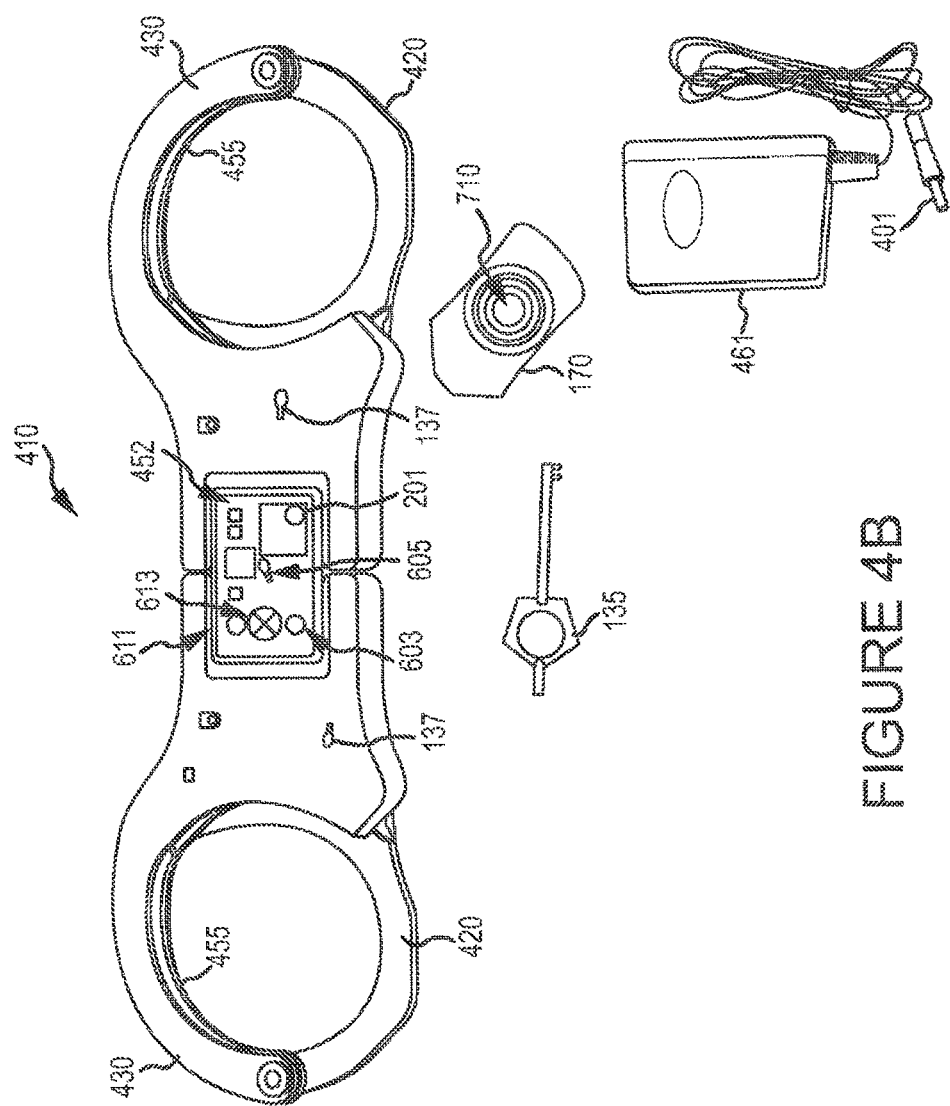
FIG. 4B depicts another embodiment of the restraining device in accordance with systems and methods consistent with the present invention, as shown with a tool/key, activation controller, and charger.
Figure 4C:
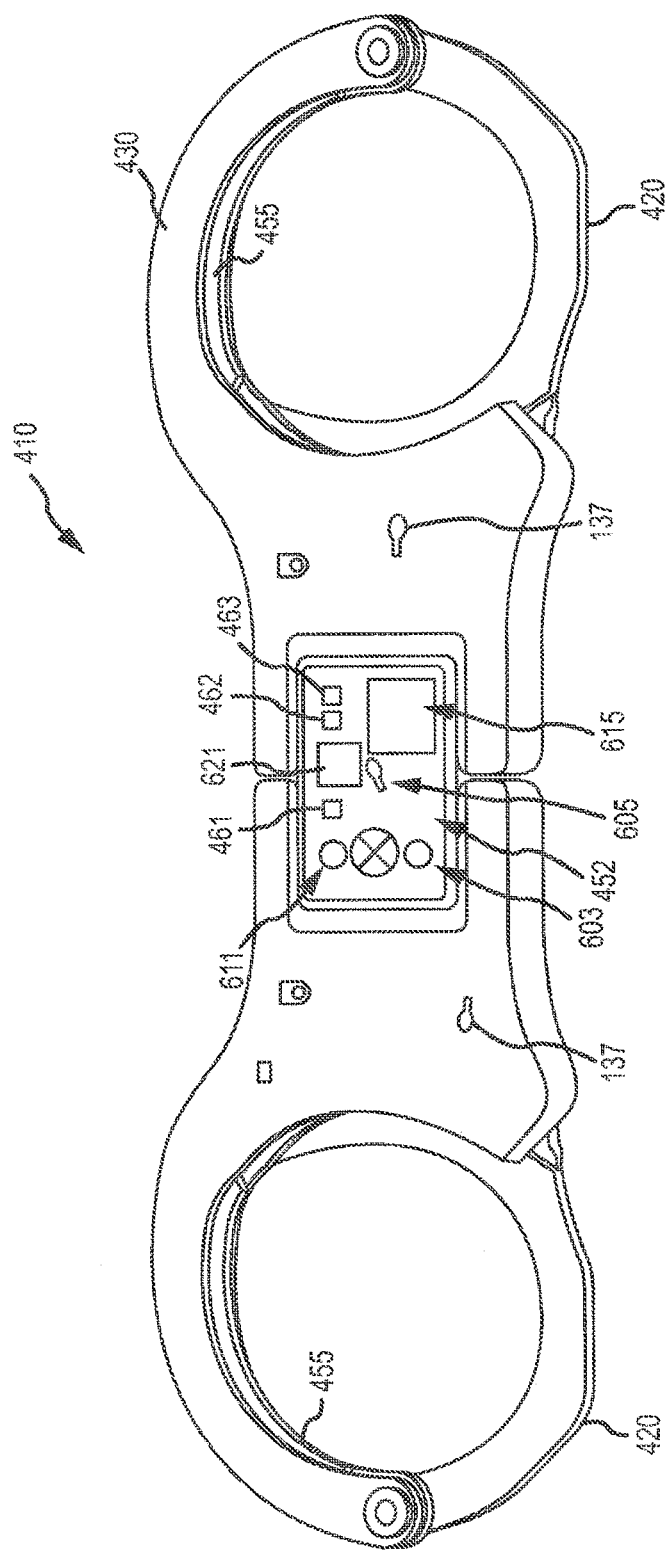
FIG. 4C shows a top plan view of the restraining device of FIG. 4B, with an exemplary component layout.
Figure 4D:
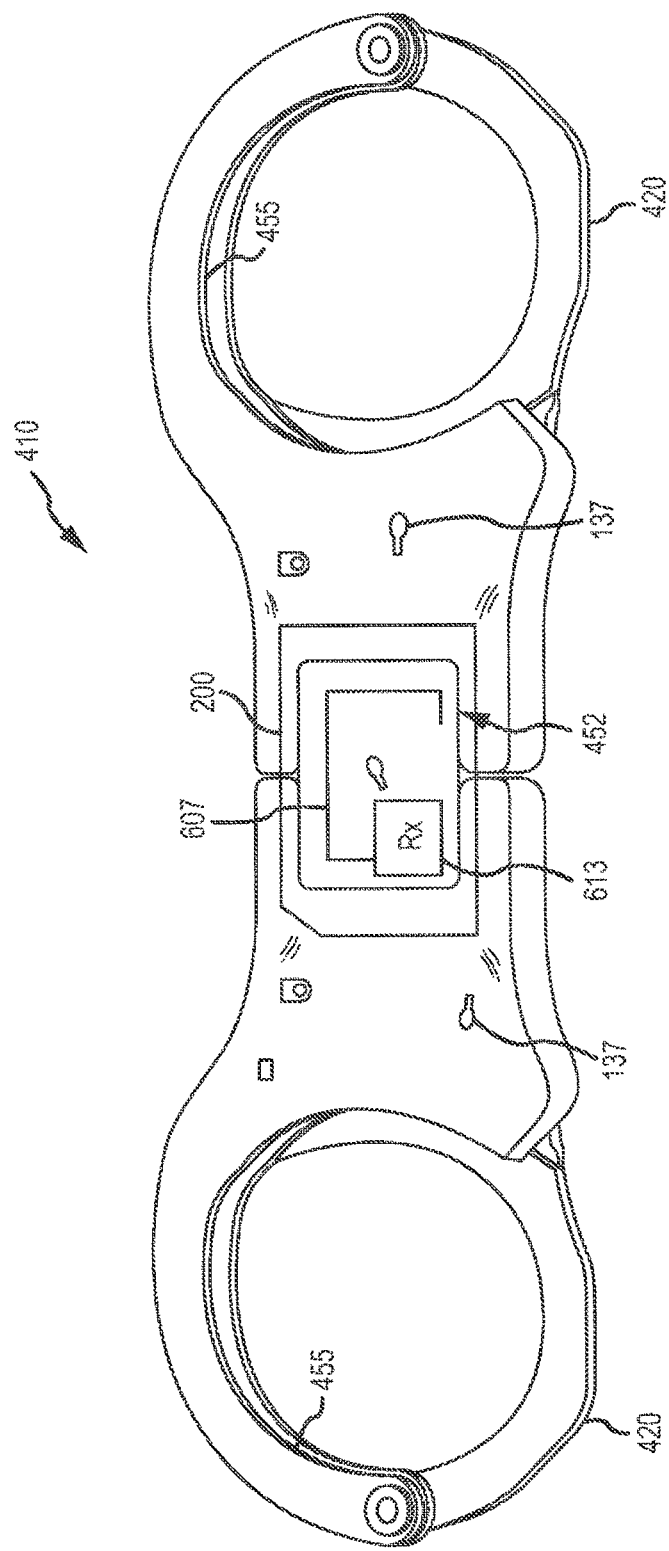
FIG. 4D shows a bottom plan view of the restraining device of FIG. 4B, with an exemplary component layout.
Figure 4S:
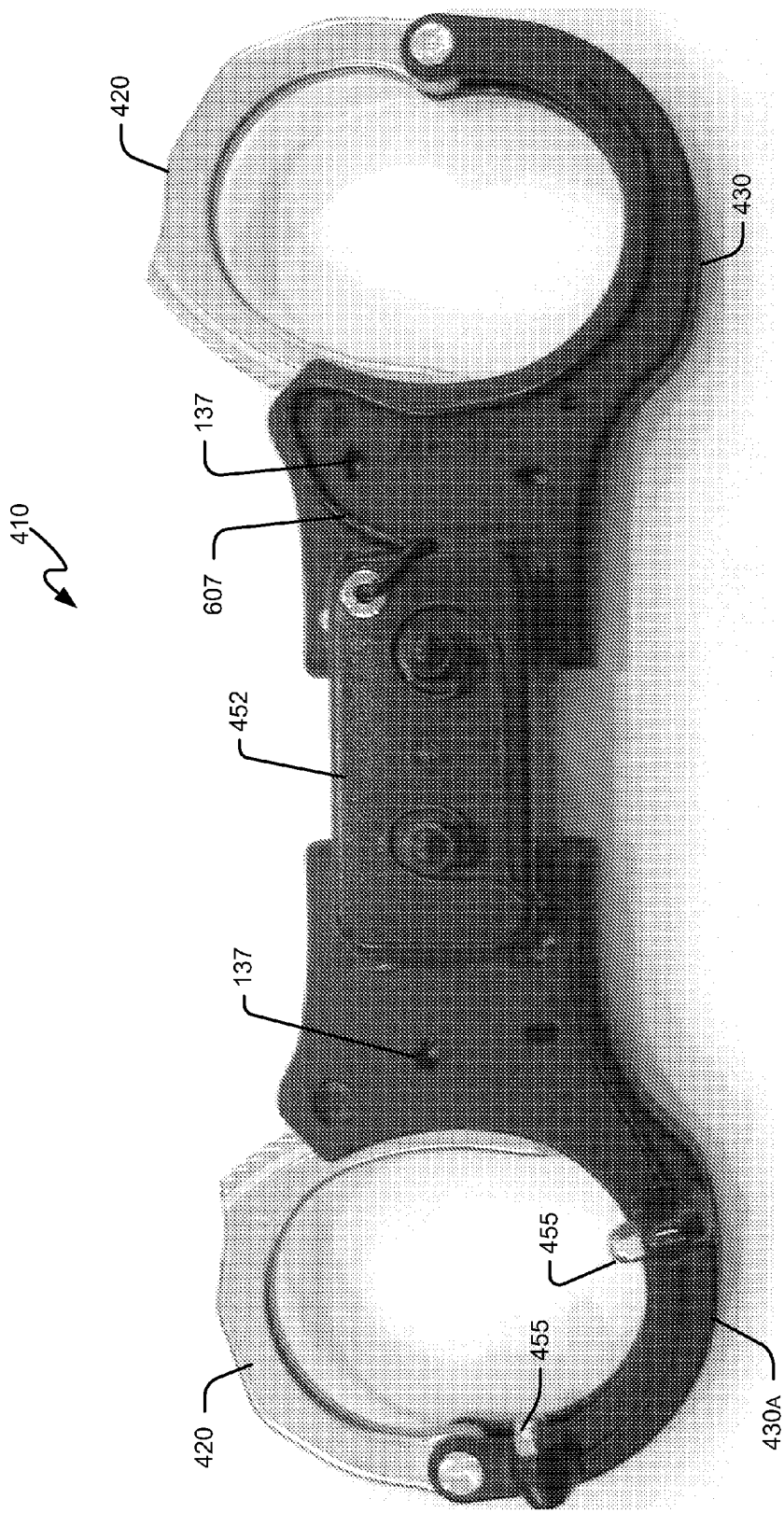
FIG. 4E illustrates a back side plan view another embodiment of the restraining device in accordance with systems and methods consistent with the present invention.
FIG. 4F shows a back side perspective view of the restraining device of FIG. 4E.
FIG. 4G shows a front side plan view of the restraining device of FIG. 4E.
FIG. 4H shows a front side perspective view of the restraining device of FIG. 4E.
FIG. 4I shows a top side plan view of the restraining device of FIG. 4E.
Figure 4F:
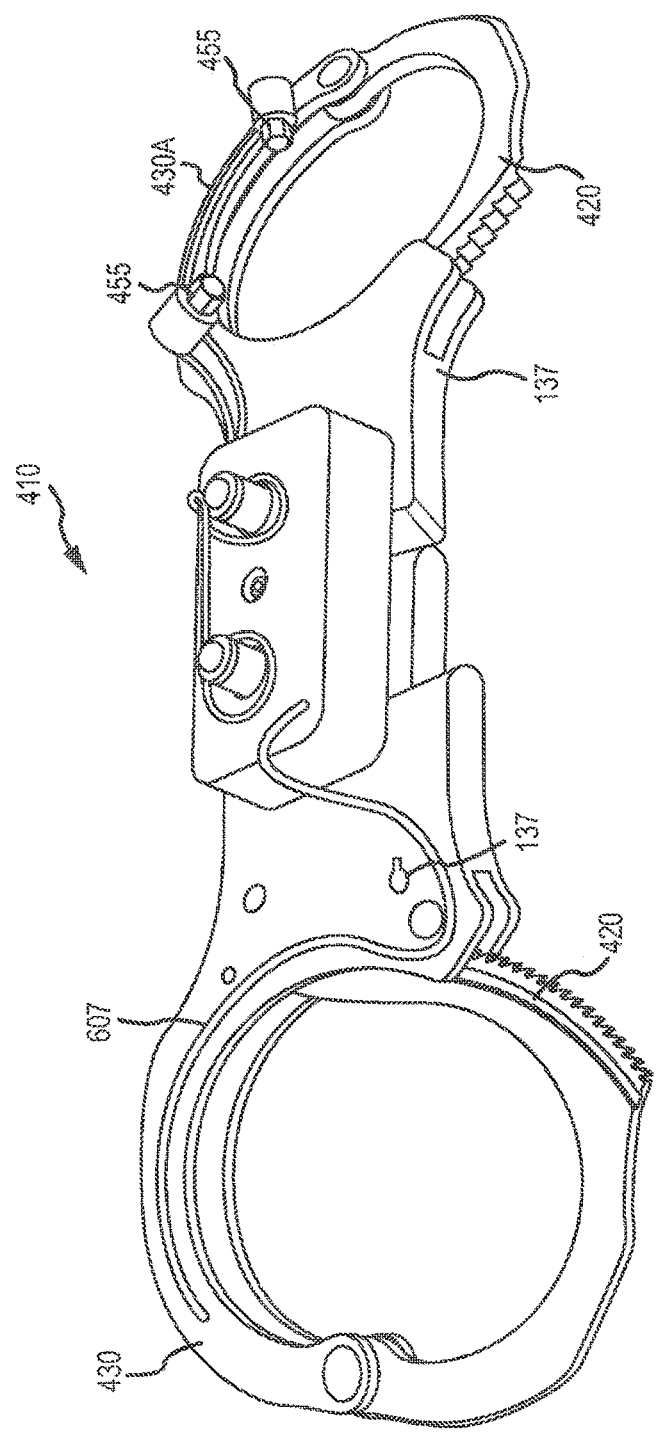
Figure 4G:
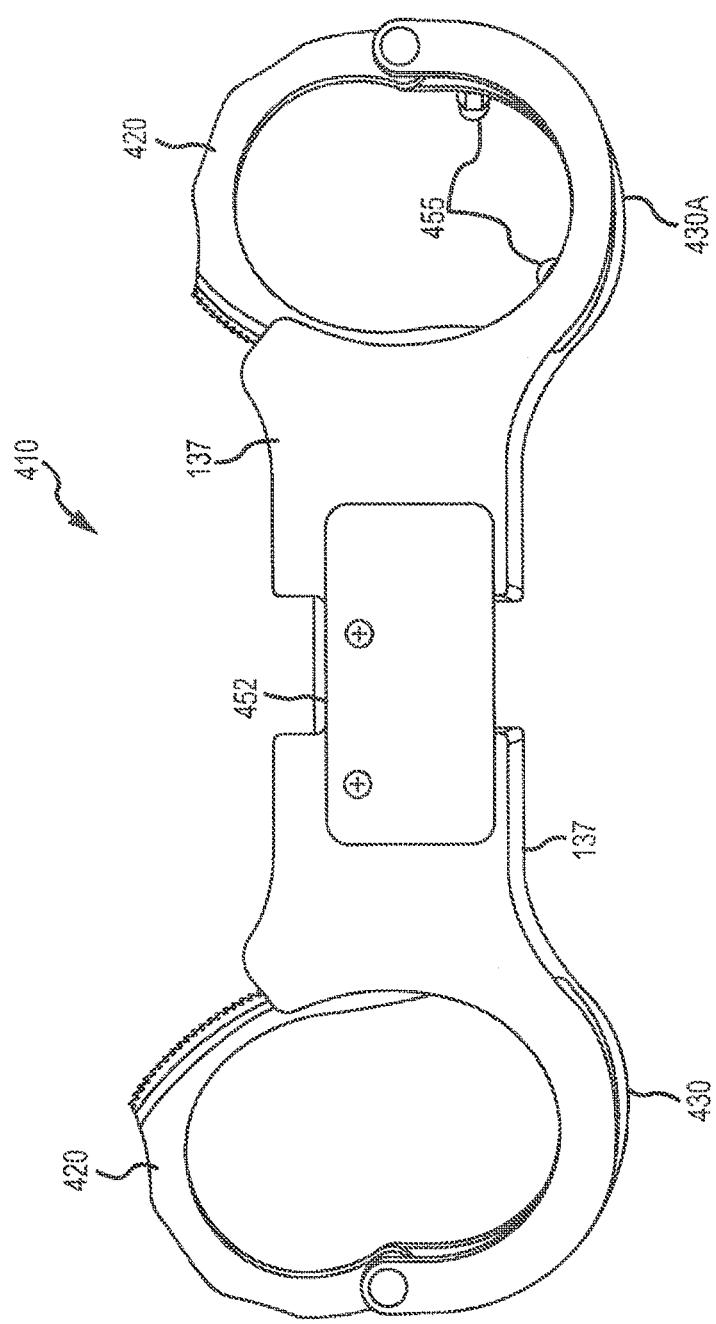
Figure 4H:
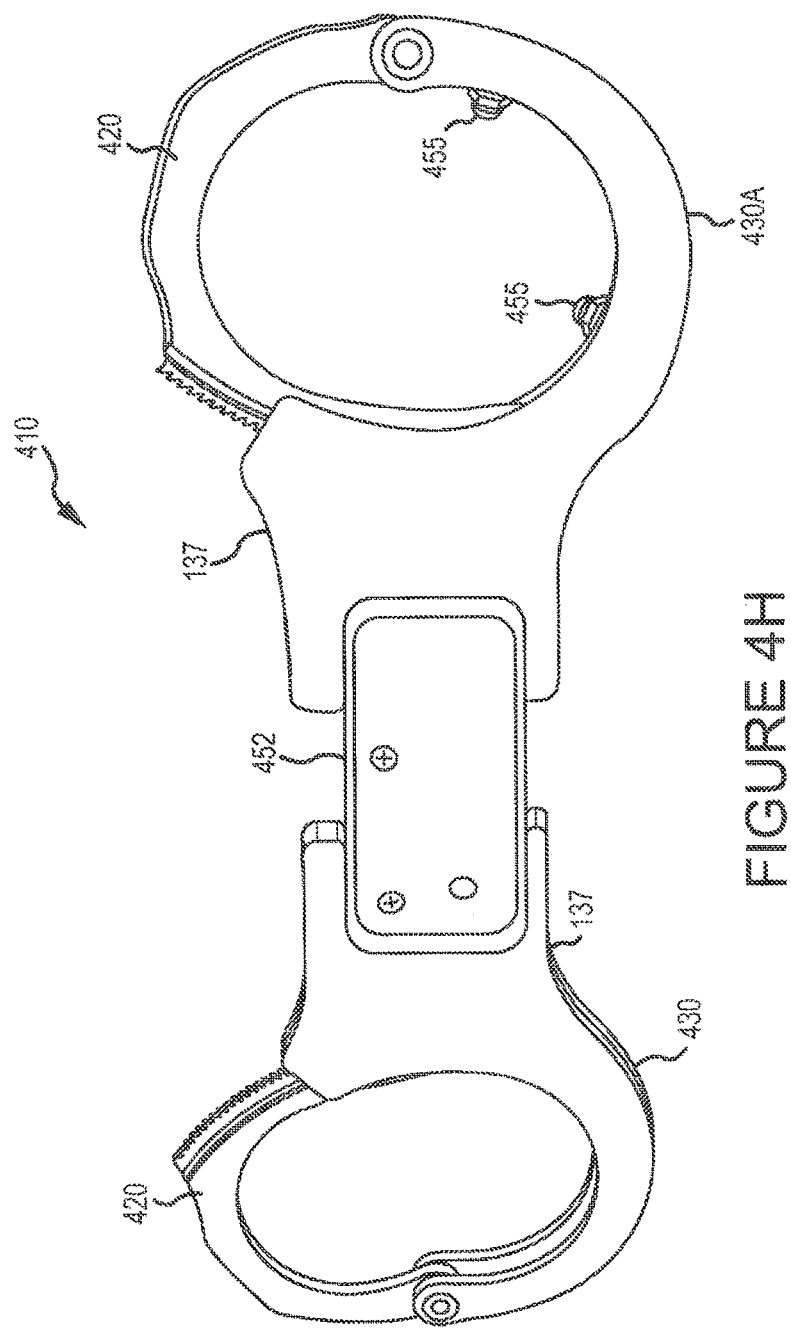
Figure 41:
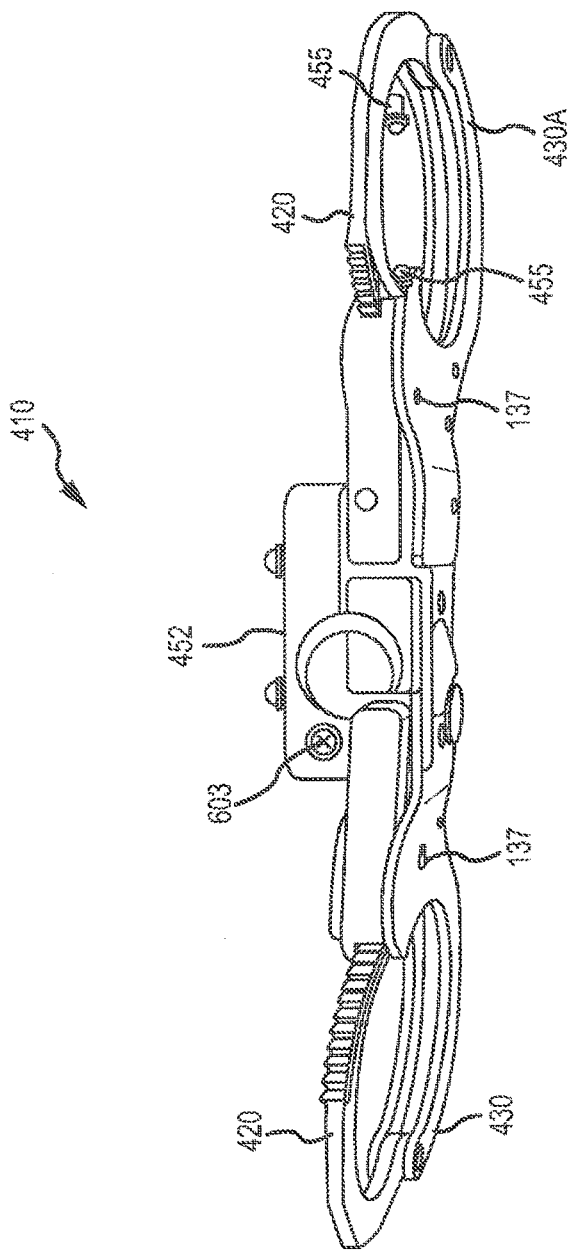

FIGS. 4B-4D show various views of an embodiment of the present invention that is similar to the implementation shown in FIG. 4A. In this embodiment, the restraining device 410 has two restraining members 420 respectively coupled to central receiving members 430. The central receiving members 430 are coupled to a central housing portion 452, wherein an electric shock component (described below) is disposed. The coupling may be provided by any desired means, and in one embodiment, a hinge coupling allows for improved wearing comfort by the detainee by allowing for freedom of movement or positioning. Any suitable number of electrodes 455 are situated within the central receiving members 430, and in the illustrated embodiment, one electrode strip, preferably flexible, is situated in each inside area of the central receiving members 430. Restraining device 410 may be used on various portions of the body but is preferably configured for use on for use on a detainee's wrists.

The central housing portion 452 also provides for a switch mechanism 605 that may be actuated in an on/off manner by tool 135 to respectively energize or de-energize the electric shock component disposed within the housing portion 452. In some embodiments, the same tool 135 that actuates the switch mechanism 605 also operates locking mechanisms 137 to allow selective opening and closing of restraining members 420, thereby allowing attachment to or release from portions of a detainee's body (or alternatively, between a portion of the detainee's body and an anchor point such as a wall hook, a seat, or a piece of furniture). In one embodiment, when the electric shock component is energized in a ready-for-use state and a power source such as a battery 200 within the housing portion 452 is supplying power, an output device 603 such as a light emitting diode may illuminate, therefore informing a detention officer that the electric shock component is armed and ready for actuation. Any color or lighting configuration may be utilized, and in one embodiment, output device 603 is a green light emitting diode.

Also shown on the housing portion 452 is a charging jack port 201, which may be any size or configuration desired to supply charging current to a power source 200 disposed within or otherwise coupled to the housing portion 452. In implementations where a charging jack is used, charging current may be provided by a conventional charging device 461 and coupled to the power source 200 through a jack 401 inserted into the charging jack port 201. In alternate embodiments, the power source 200 may be charged by an inductive interface, which provides for receiving charging current through an inductive coil without the need for a physical contact with charging wires or electrodes. In such an inductive charging configuration, charging jack port 201 may be omitted from the housing portion 452.

A portable remote-type controller 170 is also shown, and is described in more detail below. In one embodiment, when a button coupled to a switch 710 within the controller 170 is depressed, the controller transmits an actuation signal to an antenna coupled to the restraining device 410, whereupon an electric shock may be delivered to a detainee to whom the restraining device 410 is attached. When a shock is being administered or is about to be administered, warning light 611 may illuminate to show operation or impending operation, and in one embodiment, warning light 611 is an output device such as a red light emitting diode. Also, in various embodiments, an audio output device 613 may be utilized to generate a warning tone or an actuation confirmation tone to respectively warn the detainee that a shock is imminent or to advise the detention officer administering the shock that a shock is being generated and delivered to the detainee. Alternative modes of operation of the controller 170 and restraining system are discussed in more detail below.

FIGS. 4C and 4D illustrate respective top and bottom plan views of the restraining device 410 of FIG. 4B, with an exemplary component layout being shown for elements of the shock generator component 150 disposed within or on the housing portion 452. While circuit components are shown through the housing for ease of illustration, it is expected that most components will be securely disposed entirely within the housing portion 452, or securely mounted to the housing portion 452. For example, a high voltage DC/DC converter 615 and spark gap 621 are located in the housing portion 452, as are high voltage capacitors 461, 462, and 463, microcontroller/logic component (not shown) and receiver and/or transceiver component 608. Some components such as power source 200 (which in an embodiment may comprise a substantially flat lithium-ion rechargeable battery) or antenna 607 may be mounted in a conformal manner on an outside surface of the housing portion 452 or on any other internal cavity or external surface of restraining device 410.

FIGS. 4E-4I show various views of an embodiment of the present invention that is similar to the implementation shown in FIGS. 4B-4D. In this embodiment, the restraining device 410 has two restraining members 420 respectively coupled to central receiving members 430. The central receiving members 430 are coupled to a central housing portion 452, wherein an electric shock component (described below) is disposed. Any suitable number of electrodes 455 are situated within the central receiving members 430, 430A, and in the illustrated embodiment, one side of the central receiving members 430A has electrodes 455 disposed in an interior portion. Restraining device 410 may be used on various portions of the body but is preferably configured for use on for use on a detainee's wrists.

The central housing portion 452 also provides for a switch mechanism that may be actuated in an on/off manner by a tool such as a key to respectively energize or de-energize the electric shock component disposed within the housing portion 452. In some embodiments, the same tool 135 that actuates the switch mechanism also operates locking mechanisms 137 to allow selective opening and closing of restraining members 420, thereby allowing attachment to or release from portions of a detainee's body (or alternatively, between a portion of the detainee's body and an anchor point such as a wall hook, a seat, or a piece of furniture). In one embodiment, when the electric shock component is energized in a ready-for-use state and a power source such as a battery within the housing portion 452 is supplying power, an output device 603 such as a light emitting diode may illuminate, therefore informing a detention officer that the electric shock component is armed and ready for actuation. Any color or lighting configuration may be utilized, and in one embodiment, output device 603 is a green light emitting diode. Also shown in FIGS. is an antenna 607 which in various embodiments is enclosed within the central receiving members 430, 430A to protect it from damage.

Figure 5:
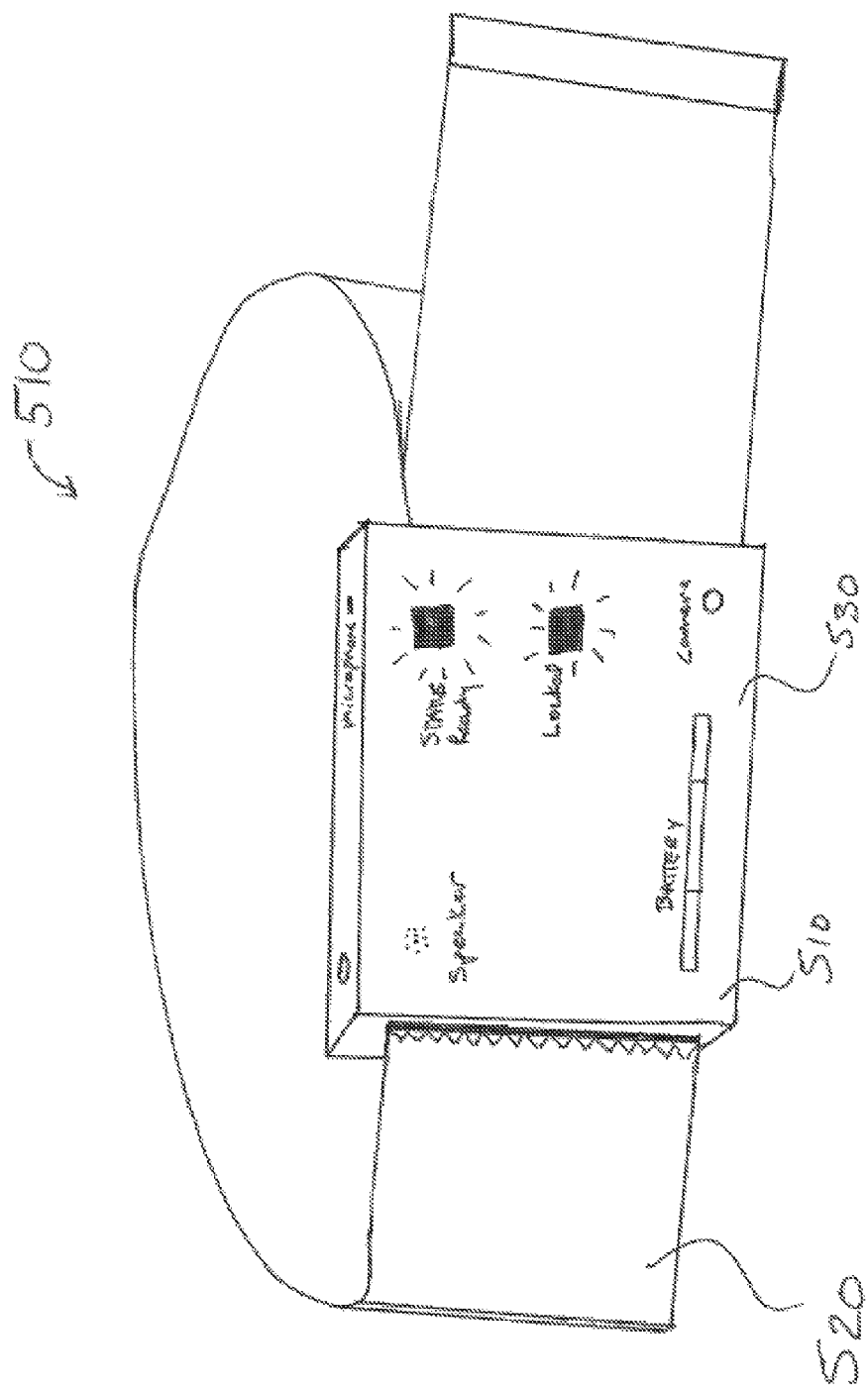
FIG. 5 depicts another embodiment of the restraining device in accordance with systems and methods consistent with the present invention.

Another embodiment of the restraining device of the present invention is shown in FIG. 5. The restraining member 520 is comprised of fabric with embedded metal wires to prevent cutting of the fabric. When device 510 is in a first position the restraining member 520 may be uncoupled from one end of the receiving member 530 similar to the operation of a belt. This restraining member 520 is circumferentially wrapped around a body part of a detainee and inserted through and/or to the receiving member 530. Once inserted into the receiving member 530, the restraining member 520 is ratchetably secured in place at the detainee and/or controller 170 operators desired location. The restraining member 520 is designed to circumferentially surround the provided portion of a detainee's body when in a closed position. Additionally, once the restraining member 520 is inserted into the receiving member 530 the restraining member 520 is not able to be loosened or removed from the receiving member without introduction of a tool or key. The width of the restraining member 520 is any suitable width and thickness and may vary with material. For instance, a restraining member 520 made from fabric may be about 5 centimeters in width and may be about 3 millimeters thick. Electrodes, 555 preferably two, (not shown) extend from the rear surface of the receiving member 530 of restraining device 510. In one embodiment these electrodes are in constant contact with the detainee. The receiving member 530 may be made in any suitable shape for containing the device elements and securing the positioning of restraining member 520 such as spherical, cylindrical, cubic, conical, or ellipsoid. In the preferred embodiment receiving member 530 is substantially rectanguloid with a rectangular front face. Its dimensions may be any suitable dimensions, but in the preferred embodiment it is 4 inches long, 2.5 inches tall and 0.5 inches thick. A coupler for coupling to additional restraining devices is shown in FIG. 5. Device 510 may also comprise one or more of a speaker, status indicators, such as battery level, locked or unlocked status, antenna, audio sensor, video sensor, an agitator for producing vibration, power source, electric shock component, memory, and/or control system (all described below).

In some embodiments, the restraining member 120 may not be disengaged from the receiving member 130 while in the closed position until a tool 135 is engaged in and actuates a locking mechanism 137 and/or a code is entered through an input-output interface in the restraining device. Any suitable tool 135 or combination of tools and/or code may be used to disengage the receiving member 130 and the restraining member 120 such as a cut key; a double sided key; a four sided key; a cylinder key; an electronic signal; a magnetic signal; a punch code; a transponder key; an RFID key; a biometric measurement; a finger print, and voice recognition activated software. In the preferred embodiment a physically coded key may be utilized to disengage the restraining member 120 from the receiving member 130. For security, in some embodiments, only one tool 135 (plus any required backup tools) may operate a matched restraining device 110. In other embodiments, a back-up physical tool and/or an electronic signal may allow movement of the restraining member 120 from a closed position to an open position. For instance, in one embodiment a controller 170 must first be set to a "safe to unlock" designation and communicate this designation with restraining device 110 prior to a tool 135 successfully moving the restraining member 120 from a closed position to a first open position.

In some embodiments status indicators on restraining device 110 indicates device availability, closed/locked position and/or battery charge remaining. In preferred embodiments the status indicators include one or more of colored light emitting diodes where different colors or patterns correspond to different status states.

The shock generator component 150 is coupled to restraining device 110. This may be accomplished through any suitable coupling such as welding, epoxy, mechanical fasteners, snap fit, and pressure fitting, however, the shock generator component 150 is preferably enclosed within a sealable secure housing 152 of the restraining device 110. In one embodiment this sealable secure housing 152 portion is accessible through the use of a specialized tool that acts upon a tamper-resistant fastener such as a torx fastener with internal pin, a hex key faster with internal pin, snake-eye spanner fasteners, and the like. Through the use of such a specialized tool-fastener closure in the housing 152, the detainee to whom the restraining device 110 is attached cannot easily access and deactivate the electric shock component 150 or power source 200. An included gasket may assist in making the secure portion water tight and weather proof. In yet another embodiment, components of the restraining device 110 such as the electric shock generator, sensors and I/O 1004, control system 160, and power source 200 may be entirely or partially permanently sealed within a non-accessible portion of the housing 152. By permanently sealing such components in the housing (such as by epoxy or other potting compound), the restraining device may be configured to be resistant to environmental concerns while resisting attempts at disablement by the detainee to whom the restraining device is attached.

Electric Shock Component 150 and Detainee Interface/Electrodes 155

In one embodiment, electric shock component 150 is capable of delivering a scalable nonlethal electric shock to a detainee. The level of shock may be internally preset and fixed or it may be a selectable value by a detention officer or an external controlling entity 1100 utilizing a controller 170 configured to adjust deliverable shock. The electric shock component 150 delivers shock through a detainee interface 155 such as one or more electrodes. In some embodiments, the detainee interface or electrode 155 may be retracted until needed for delivery of electric shock or may be in constant contact with a portion of the detainee. In various embodiments electrodes may be barbed, sharp, blunt, smooth or have any other suitable surface characteristic for delivering an electric shock. Electrodes may comprise a point of shock delivery or may comprise a band of shock delivery that travels along at least a portion of the inside surface of the restraining device. This band may have alternating electrode portions which constitute a spark gap for receiving a conductor, such as a portion of a detainee's body.

Alternatively, nonconductive material may be disposed between portions of the electrode band to comprise a suitable spark gap. In another embodiment the electric shock component 150 includes electrode nodes spaced approximately equally around the interior surface of the restraining member 120 and/or receiving member 130 making contact with a detainee's skin. In the preferred embodiment the electrode is at least one (preferably two) fixed smooth raised surfaces located on the interior surface of the restraining member 130. The electrode 155 may be made of any suitable conductive material such as metal and in the preferred embodiment comprises copper.

Through they may be separated by any suitable distance, in the preferred embodiment the plurality of smooth raised surfaces of the electrodes are about 2 inches apart on an inside surface of either the restraining member 120 and/or the receiving member 130. In this configuration, electrodes 155 are in constant contact with a provided portion of detainee while restraining device 110 is in a closed position. An insulator coats at least the surface of the restraining member 130 of at least the air gap proximity of the fixed smooth raised surface of the electrode 155. The smooth raised surface of the electrode is not covered by an insulator. This insulator 230 prevents the electrical shock from being directed into conductive portions of restraining device 110 rather than the detainee. The insulator 230 may be made out of any suitable insulating material such as latex, vinyl, or nitrile rubber, glass, graphite, PTFE, and the like, but preferably comprises a rubber coating and/or layer.

The level of shock delivered by the electrodes to the detainee may be any suitable voltage level such as between 20,000 and 150,000 volts. In the preferred embodiment an electric shock of about 100,000 volts is delivered to a portion of a detainee's body. The level of shock may be any suitable ampere level such as between 0.5 and 6 milliamps. In the preferred embodiment an electric shock at about 3 milliamps is delivered to a portion of a detainee's body. In various embodiments, the duration of the shock is selectable. Though the shock may last for any desired period, in the an embodiment the shock is delivered between about 1 and 4 seconds and in another embodiment, between 0.5 and 10 seconds. The delivery of the electric shock may be a pulsed frequency or constant.

Figure 6A:
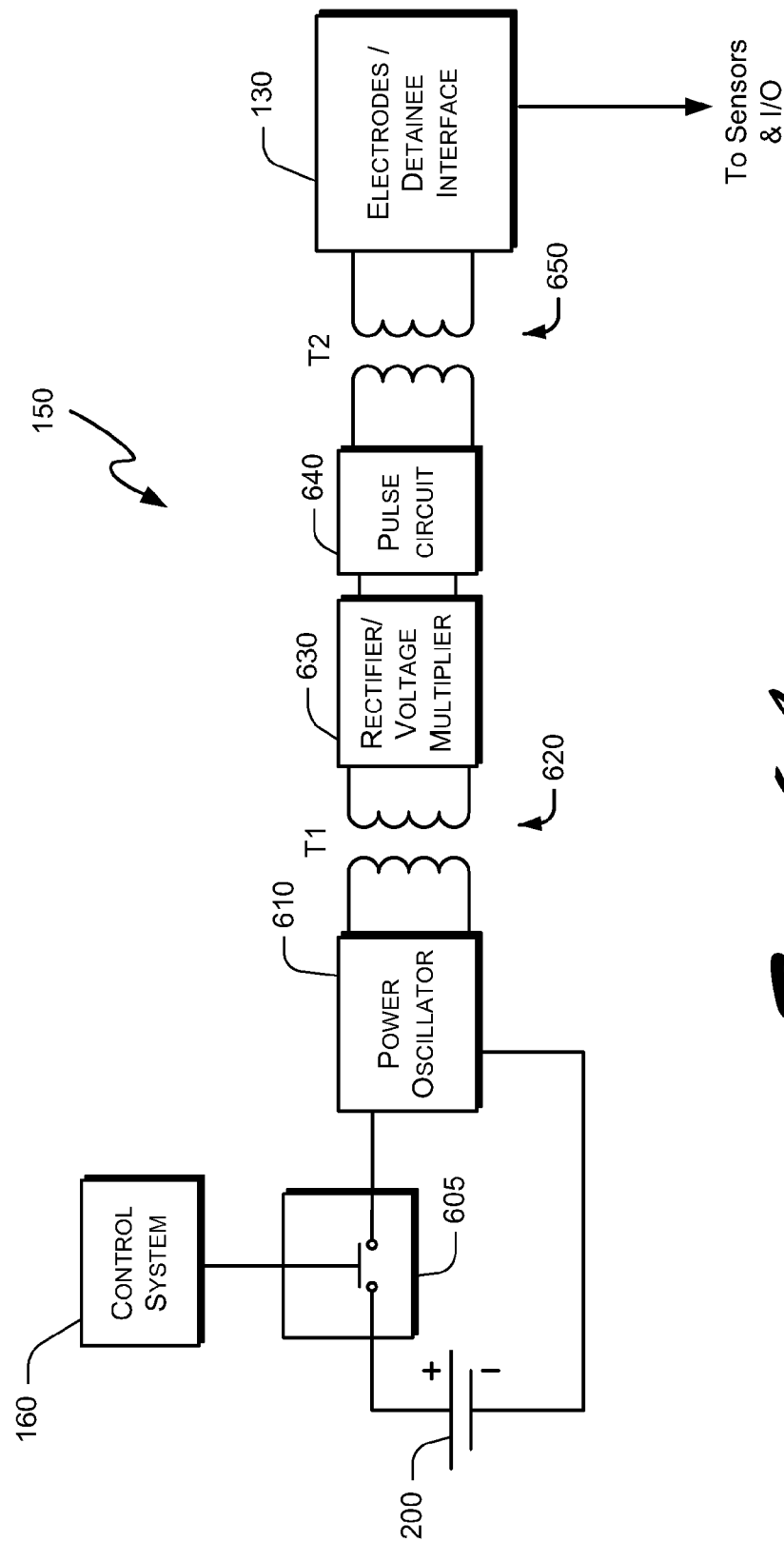
FIG. 6A depicts a block schematic diagram of one embodiment of an electric shock component of the restraining device of the present invention.

FIG. 6A illustrates an embodiment of the electric shock component 150 of the present invention. The electric shock component's power source 200 is powered preferably by one or more batteries. The power source 200 is selectively switched 605 by the control system 160 to energize the circuit 150 when the control system determines that a shock is to be administered to the detainee. Those of skill in the art appreciate that switch 605 may comprise an electronic switch, a relay, a solenoid, or any conventional means to controllably switch power to the electric shock component circuit. Once the switch 605 is actuated to provide power, the batteries energize an oscillator 610 to produce a specific pulse pattern of electricity (AC or pulsed DC). Coupled to the oscillator 610 is a first transformer 620 that initially steps up the voltage supplied by the power supply, correspondingly lowering the amperage of the current produced at its output.

Coupled to the first transformer 620 is a rectifier/voltage multiplier circuit 630 that rectifies the current output from the first transformer 620 and may further store energy by components such as capacitors. When activated, a pulse circuit, or spark gap switches the DC power from the rectifier/voltage regulator 630 on and off and supplies the pulsed current to the primary of a second transformer 650. The second transformer 650 again acts to step up voltage while correspondingly reducing current. This pulsed high voltage/low current output from the second transformer 650 is coupled to the electrodes/detainee interface 155 for delivering an electrical shock to a detainee. In some embodiments, one or both of the transformers 620, 650 are insulated, such as with vacuum potted epoxy resin to prevent internal shorting. The pulse circuit 640 may comprise a spark gap, triac, diac, SCR, or other component to pulse the input current to transformer 650 to clip the output voltage to a predetermined level. A plurality of capacitors and/or batteries may be implemented in series or parallel to provide additional energy storage capacity or discharge. If desired, the power source 200 may be rechargeable and/or replaceable. As mentioned previously, recharging may be provided through an inductive coupling or through a wired contact to an additional power entity.

The electric shock component 150 may be activated by any desired actuator such as an integrated control system 160, discussed below. In various embodiments, actuation may occur by remote control, computer program, button, trigger, voice activated command, wired control, and/or a combination thereof. In the preferred embodiment the electric shock component 150 is controlled by a remote control 170, discussed below.

Figure 6B:
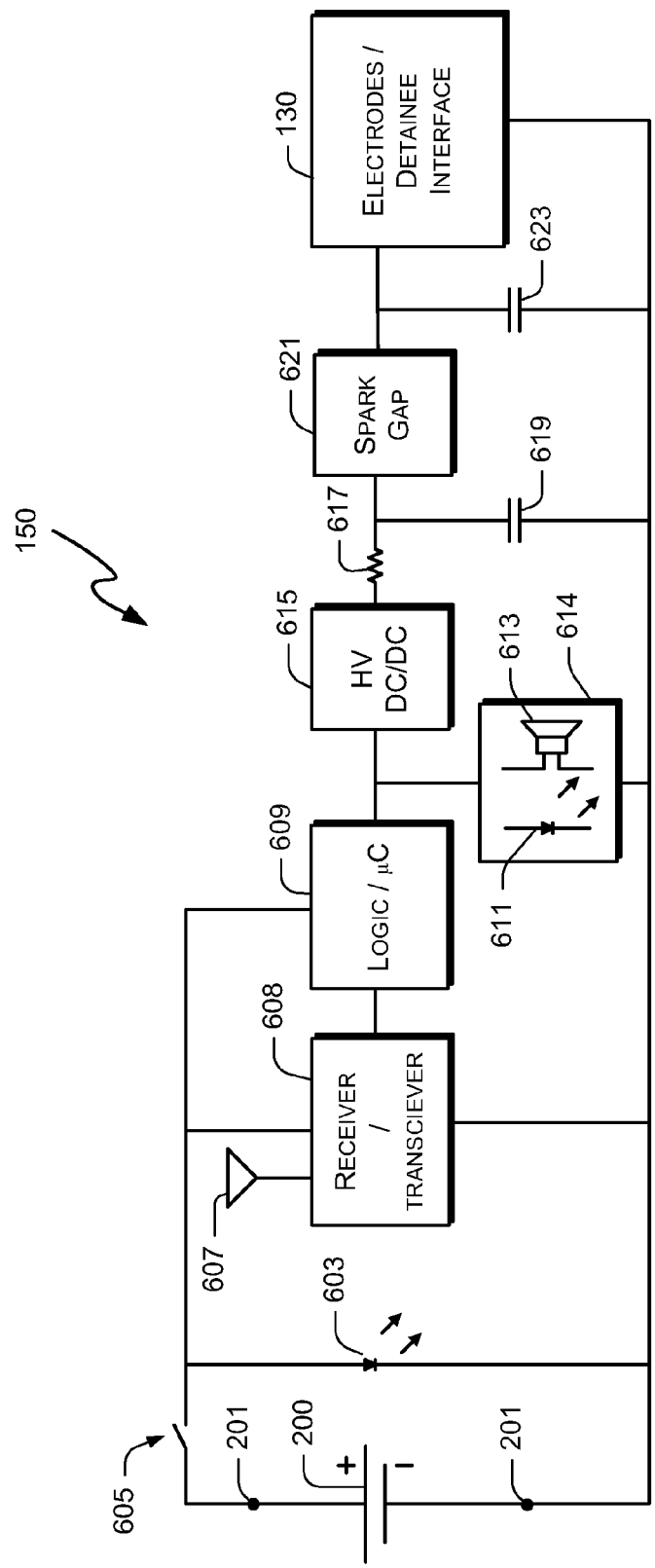
FIG. 6B depicts a block schematic diagram of another embodiment of an electric shock component of the restraining device of the present invention.

Another embodiment of the electric shock component 150 of the present invention is illustrated in FIG. 6B. The electric shock component's power source 200 is powered preferably by one or more batteries. Charging terminals 201 are provided so that power source 200 may receive charging current; alternatively, charging terminals may be coupled to an inductive charging interface (not shown) so that the power source 200 may be charged in a contactless manner. The power source 200 is selectively switched 605 by an external entity such as a detention officer to energize the circuit 150 and transition the restraining device from a quiescent mode to an active mode. Those of skill in the art appreciate that switch 605 may comprise an electronic switch, a relay, a solenoid, or any conventional means to controllably switch power to the electric shock component circuit, and may comprise a switch that is mechanically actuated through a tool or key inserted into the restraining device. Once the switch 605 is actuated to provide power, the batteries energize the transceiver/receiver 608, a logic/microcontroller block 609, and a light output device 603 such as a light emitting diode to indicate that power is being applied to the circuit 150.

Once powered, the receiver/transceiver 608 and the logic/microcontroller 609 to which it is coupled monitor wireless signals received by antenna 607, and if an activation signal is received that meets a predetermined frequency, amplitude, encoding or other condition, the logic 609 initiates generation of a shock through the HV DC/DC component 615. The restraining device may have outputs 614 such as a light element or light emitting diode 611 or speaker/transducer 613 to alert and/or confirm that a shock is being administered. Alternatively, the output may be configured to deliver a warning so that a detainee to whom the restraining device is attached may be given an opportunity to cease an undesired behavior and thereby have administration of a shock cancelled by the detention officer.

Output from the high voltage DC/DC converter 615 is coupled through a resistor/capacitor network (617, 619) to a spark gap 621. Resistor 617 and high voltage capacitor 619 may comprise any suitable values, and in one embodiment may be implemented with approximate respective values of 1.5 MΩ and 2.5 µf. A high voltage filter capacitor 623 is coupled to the output of the spark gap 621, which is in turn coupled to the detainee interface 130 which may comprise electrodes that are in approximation with a portion of detainee's body.

The electric shock component 150 may be activated by any desired actuator such as an integrated control system 160, discussed below. In various embodiments, actuation may occur by remote control, computer program, button, trigger, voice activated command, wired control, and/or a combination thereof. In the preferred embodiment the electric shock component 150 is controlled by a remote control 170, discussed below.

Figure 6C:
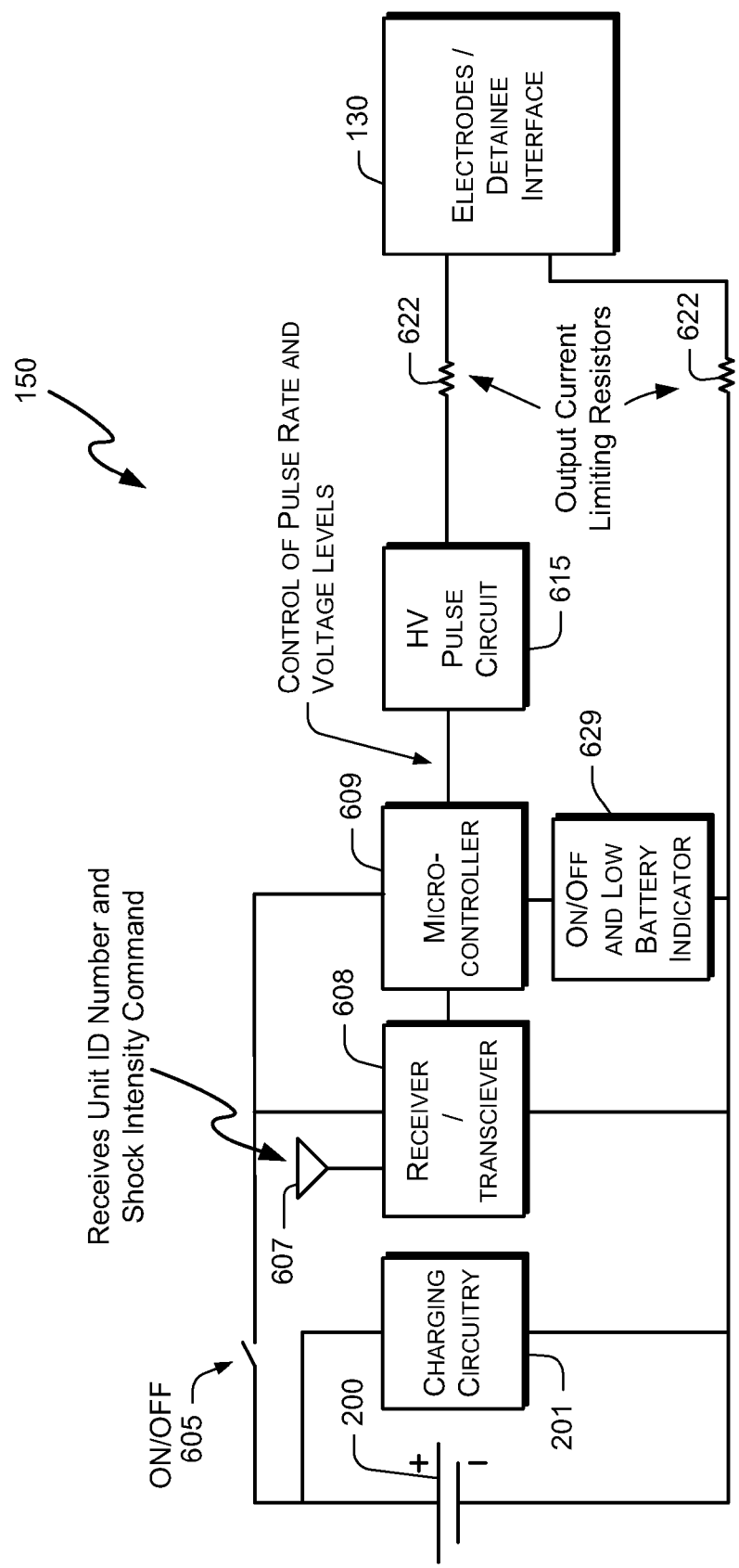
FIG. 6C depicts a block schematic diagram of yet another embodiment of an electric shock component of the restraining device of the present invention.

Another embodiment of the electric shock component 150 of the present invention is illustrated in FIG. 6C. The electric shock component's power source 200 is powered preferably by one or more batteries. Charging circuitry 201 is provided so that the power source 200 may receive charging current; charging circuitry 201 may include, for example, terminals for coupling to an external charging jack; rectifiers and voltage regulators; intelligent overcharge limiting circuitry; a contactless inductive charging interface; and combinations thereof. The power source 200 is selectively switched 605 by an external entity such as a detention officer to energize the circuit 150 and transition the restraining device from a quiescent mode to an active mode. Those of skill in the art appreciate that switch 605 may comprise an electronic switch, a relay, a solenoid, or any conventional means to controllably switch power to the electric shock component circuit, and may comprise a switch that is mechanically actuated through a tool or key inserted into the restraining device. Once the switch 605 is actuated to provide power, the batteries energize the transceiver/receiver 608 and a microcontroller/processor 609.

Once powered, the receiver/transceiver 608 and the logic/microcontroller 609 to which it is coupled monitor wireless signals received by antenna 607, and if an activation signal is received that meets a predetermined frequency, amplitude, encoding or other condition, the logic 609 initiates generation of a shock through the high voltage pulse circuit 615. For example, the encoding or other condition may comprise a unique unit ID number, and if the microcontroller 609 determines that the received unique unit ID number matches an ID number of the restraining device previously stored within a memory coupled to the processor (not shown), then the microcontroller 609 proceeds with generation of a signal to cause the high voltage pulse circuit 615 to generate one or more shock pulses. Through analysis of the unit ID number received through the receiver 608, the restraining device may be operated selectively in an environment where multiple detainees are fitted with restraining devices of the present invention, allowing, for example, a detention officer to transmit an activation signal that will cause a shock to be delivered to one of a group of detainees. Alternatively, multiple IDs may be encoded in the controller's output signal, allowing a plurality of devices to be activated.

In an implementation, in addition to the receiver 608 receiving a unit ID number, a voltage level command may be received and provided to the microcontroller 609. Such voltage level command allows, for example, a detention officer to select an desired shock intensity and/or duration depending on the amount of deterrence needed for any particular situation. For example, the detention officer may press a default shock level button on a controller that instructs the microcontroller 609 to output a first shock intensity; or the detention officer may otherwise operate a controller to transmit a voltage level command that when interpreted by the microcontroller, results in a second intensity and/or duration shock being applied to the detainee through the electrodes 130. The restraining device may have outputs (not shown) such as a light element or light emitting diode or speaker/transducer to alert and/or confirm that a shock is being administered. Alternatively, the output may be configured to deliver a warning so that a detainee to whom the restraining device is attached may be given an opportunity to cease an undesired behavior and thereby have administration of a shock cancelled by the detention officer. Also included in certain embodiments is an on/off and low battery indicator 629, which may comprise one or more light emitting diodes (LEDs) that may optionally be modulated with different colors to indicate different battery level or shock conditions. Output from the high voltage pulse circuit 615 is coupled through a output current limiting resistors (622) the detainee interface 130, which may comprise electrodes that are in approximation with a portion of detainee's body.

The electric shock component 150 may be activated by any desired actuator such as an integrated control system. In various embodiments, actuation may occur by remote control, computer program, button, trigger, voice activated command, wired control, and/or a combination thereof. In the preferred embodiment the electric shock component 150 is controlled by a remote control 170, discussed below.

Controller/remote Control 170

In one embodiment, a controller 170 is coupled to the control system 160 and controls the activation and deactivation of the system. This coupling may be by any suitable manner such as by wired or wireless connection. In the preferred embodiment this coupling is wireless. In some embodiments the wireless coupling is achieved over any suitable network, which may include one or more of Skytel, USAM, Wyless, Sprint, Private LAN, T-Mobile, AT&T, Private VPN, Private area network (PAN), and/or Private WAN but in the preferred embodiment the coupling is by private LAN. The communication of the controller 170 and the control system 160 and/or additional computers may be achieved with any suitable protocol such as XML, SOAP over HTTP, UDDI, SMTP, binary encoding over TCP, ReFlex, WSDL, GPRS, EDGE, Mobitex, CDMA, EVDO, VSAT, wired LAN, Wired WAN, and/or message queues via Microsoft Windows MSMQ. The preferred communication protocol is simple object access protocol, or SOAP.

Figure 7A:
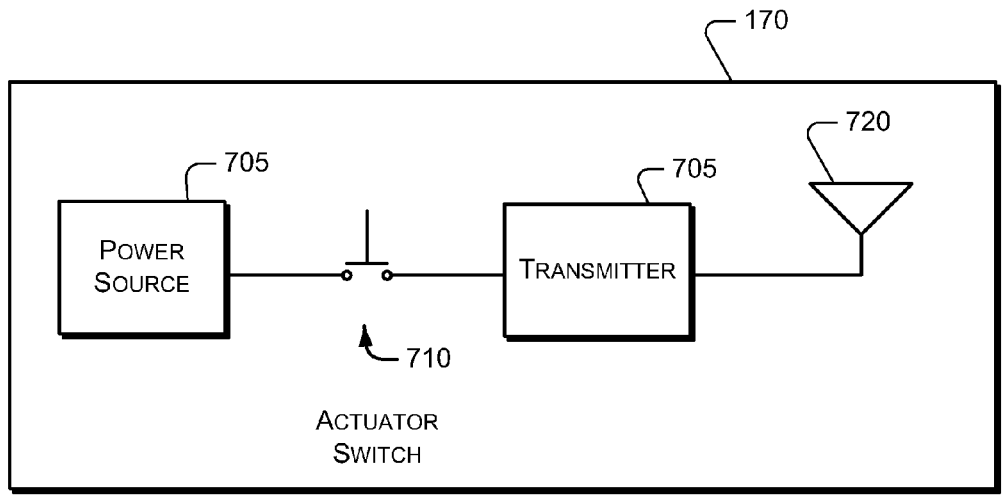
FIG. 7A depicts a schematic block diagram of a controller of the current invention.

As shown in FIG. 7A, a simple external controller 170 may comprise a power source 705 supplying power to an actuator, such as a button, switch, or trigger comprising an activation switch 710, which in turn is coupled to a transmitter 715. A preferred embodiment is a hand-held remote control. The transmitter 715 is coupled to antenna 720, and when energized by a person depressing the switch, 710, transmits an activation signal to the restraining device 110, whereupon the restraining device activates and delivers an electric shock to the detainee to whom the restraining device is attached. In various embodiments, the restraining device 110 may apply a shock only for a limited duration, or in alternate embodiments, the restraining device 110 may apply a shock continually while the activation switch is being depressed. Those of skill in the art appreciate that different or multiple switch configurations may be used, such as in implementations where multiple or progressive levels of shock are to be administered until a detainee to whom a restraining device 110 is attached is sufficiently deterred from an undesirable behavior.

Figure 7B:
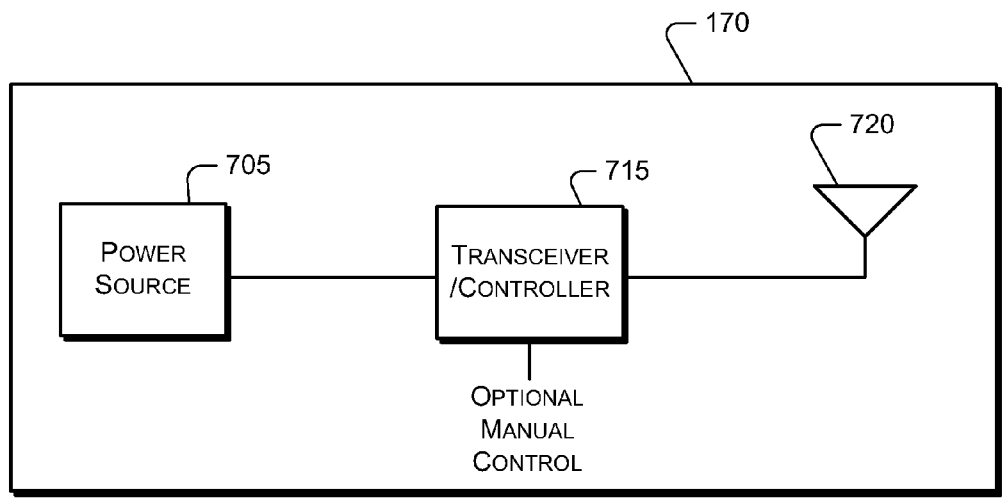
FIG. 7B depicts another schematic block diagram of a controller of the current invention.
Figure 10:
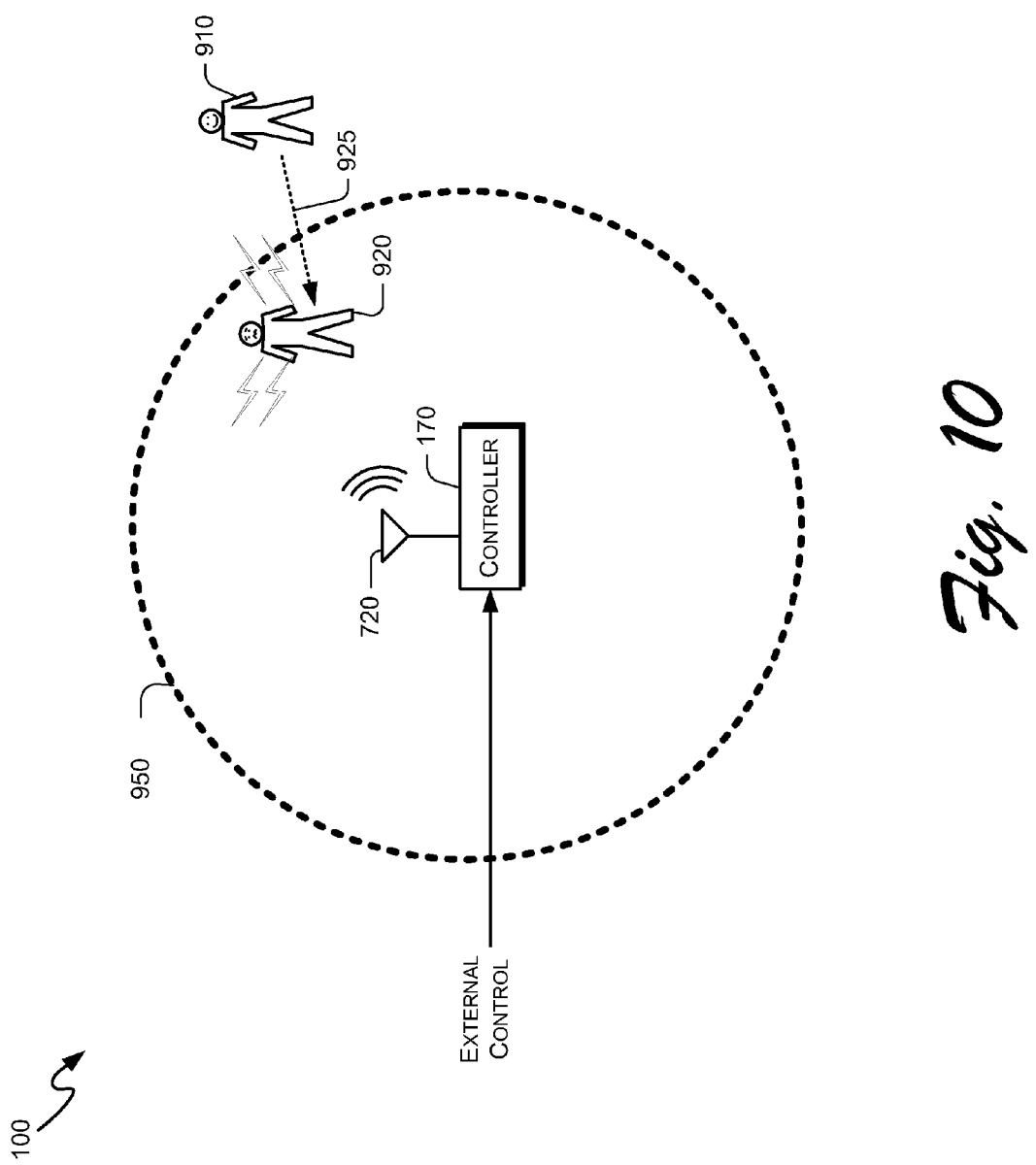
FIG. 10 shows a system of the present invention implementing a keep-out boundary for detainee restraint.

FIG. 7B shows another embodiment, wherein a "keep away" signal may be continually or intermittently transmitted from the controller 170 at a predetermined power level. In this configuration, the controller 170 becomes a device that defines an exclusion area, wherein a detainee with an attached restraining device 110 is shocked if the detainee attempts to approach the controller 170 at a distance close enough to receive a sufficient activation signal from the controller 170. FIG. 10 illustrates such a scenario where detainee 910 to whom a restraining device of the present invention is attached will not receive a shock from the restraining device unless the detainee approaches the controller, passing a predetermined keep-out boundary 950, whereupon the restraining device administers a shock to the detainee 920 who crossed the exclusion or keep-out boundary 950. Applications for this approach include low power transmitters that may be placed near security entrances, exits, and other areas where detainees are not allowed to enter or approach. In one embodiment, the transceiver/control circuit 175 may be manually actuated on or off. In another embodiment, a very low power controller 170 may be worn by detention officers or detention facility staff so that detainees that approach within a predetermined distance (0.5 to two meters, for example) would receive a shock, deterring them from approaching the person wearing the controller.

In alternate embodiments, circuit 715 comprises a transceiver that may receive an enabling signal through antenna 720 (or another antenna, not shown), instructing the transceiver in the controller 170 to transmit an activation signal thereby causing a restraining device 110 to deliver a shock to the detainee to whom it is affixed. In this manner, the controller 170 may be placed in a quiescent, non-transmitting state, awaiting an enabling signal received from an external source, such as through the antenna 720 or wired connection. Upon receiving such an enabling signal, the controller 170 begins transmitting an activation signal. When the activation signal is received by a restraining device 110 attached to a detainee that is in range of the signal being transmitted by the controller 170, the restraining device 110 delivers a shock to the detainee (or warning as described in alternate embodiments herein). Such a mode is useful to control access to a detention facility, wherein the enabling signal is terminated to allow controlled ingress/egress of detainees to the detention facility where limited power controllers are placed near entrances and exits. Once the desired detainee transfer has taken place, transmission of the enabling signal is reinstated thus providing for detainees wearing restraining devices 110 to be shocked if they approach an entrance or exit. In addition to detainee transfer, an enabling signal may be transmitted to controllers placed in other areas of a detention facility, to assist in implementing a "lock down" scenario, wherein detainees are confined to predetermined areas of the detention facility, such as their cells. In such a situation, unauthorized exit from cells without authorization will result in detainees receiving a shock by their attached restraining devices; and once the lock down condition has been terminated, transmission of the enabling signal may be terminated as well, allowing detainees again to access desired areas of the detention facility. It is also appreciated by those of skill in the relevant arts that multiple encodings or frequencies for controllers 170 may be utilized to selectively enable one or more controllers within range of the enabling signal. Such embodiment is useful, for instance, in preventing access to one part of a detention facility while allowing access to another part of a detention facility, for example, the enabling signal may be coded to activate controllers near the entrances/exits of the facility, but the enabling signal coding does not enable controllers in an exercise yard, allowing detainees selected access.

Figure 9:
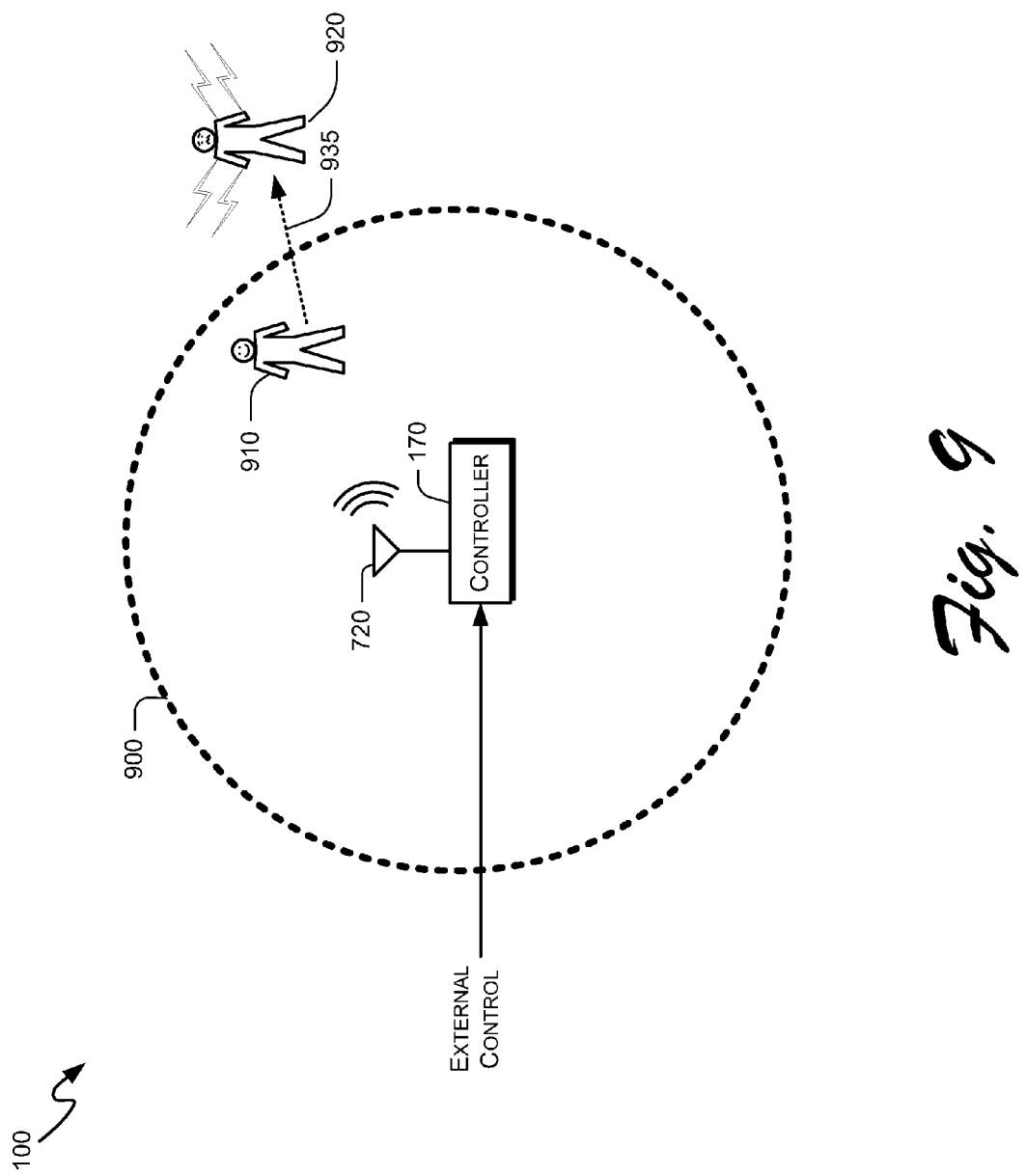
FIG. 9 shows a system of the present invention implementing a keep-in boundary for detainee restraint.

As illustrated in FIG. 9, in another embodiment, the system may be configured wherein controllers broadcast a "keep-in" signal with a predetermined power level that defines a predetermined area defined by a predetermined boundary 900 where detainees are intended to remain until an enabling signal to one or more controllers 170 is terminated (such as through a wired or wireless external control as shown in FIG. 9). In this aspect, controllers 170 and restraining devices 110 are configured to suppress application of shocks to detainees to whom the restraining devices 110 are affixed 910, as long as such detainees 910 remain in the predetermined area. In one embodiment, the controller 170 continuously transmits a deactivation signal, and retraining device 110 does not deliver a shock as long as it continually receives a deactivation signal of a predetermined power level and/or coding. In this configuration, if detainees equipped with such restraining devices 910 attempt to egress 935 the predetermined area, the egressing detainees 920 will receive a shock. Such aspects of the invention are useful in creating virtual confinement areas and are useful in prisoner transport, or other situations where escape risk is enhanced or prisoner confinement to a predetermined area (such as an area defined around a vehicle, a work area, or a detention facility area) is desired. Those of skill in the art appreciate that the boundaries shown in FIGS. 9, 10, and 11, while shown approximately circular in shape, may comprise any desired shape and may be configured base on a particular antenna and transmitter configuration within the controller 170. The size of the boundary is also not shown to any particular scale, and may be selected based on a desired region of protection or exclusion, and may be adjustable by an external controlling entity by adjusting a power level of a transmitter/transceiver within the controller 170.

As shown in FIG. 11, a combination of "keep-in" and "keep-out" transmitter configurations may combined and be used by one or more controllers 170, defining a safe zone 990 wherein a detainee 910 to whom a restraining device of the present invention is attached will not receive a shock unless the detainee crosses a predetermined keep-out exclusion boundary 950 or a keep-in boundary 900. As described elsewhere, the detainee 910 may be provided warnings as either boundary 900, 950 is approached, and a shock will not be administered unless the detainee continues to approach or pass a predetermined boundary 900, 950. The controller 170 may be configured by an external controlling entity by a wired or wireless connection, whereby a keep-in boundary function or a keep-in boundary function may be selectively enabled or disabled, for instance to allow detainee transportation into or out of the safe zone 990.

Figure 7C:
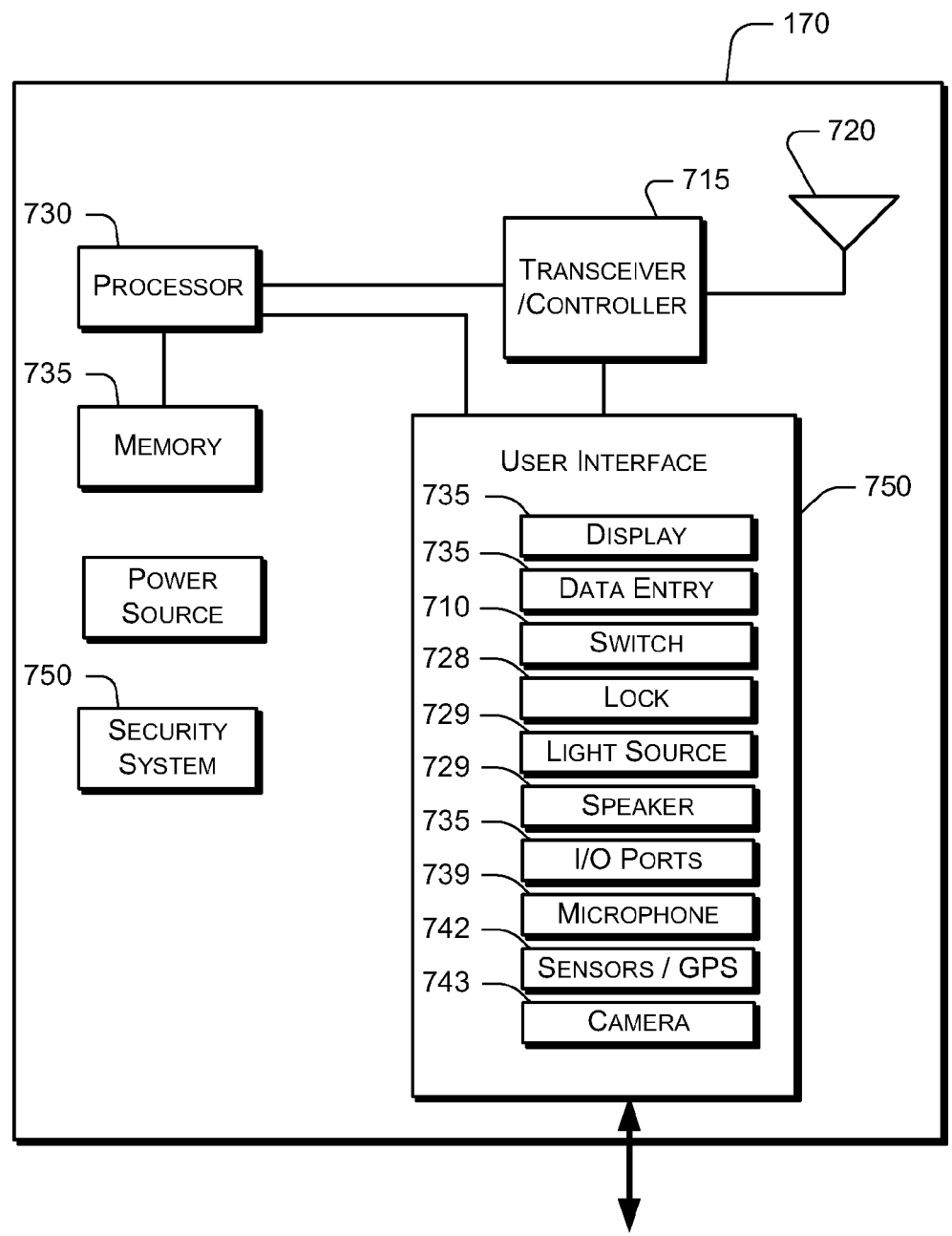
FIG. 7C depicts an alternative schematic block diagram of a controller of the current invention.

As shown in the block diagram FIG. 7C, additional embodiments the controller 170 comprise a power source 705, a transceiver 715, an antenna 720, a processor 730, a memory 735 (such as a non-volatile FLASH memory) that may be configured to store a software program, usage logs, status information, or other information. The controller 170 may be any suitable controller such a computer, internet accessible program, hand held device, microcontroller, and/ or personal digital assistant. The controller 170 may further include a user interface 725 comprising such elements as a display 726, (such as a graphic detainee interface); data entry mechanisms 727 such as buttons or a keypad; an actuator, such as a button, switch, or trigger comprising an actuation switch 710; a locking mechanism 728, a light source 729 such as one or more colored or white light emitting diodes, further optionally including one or more high-output LEDs to provide a flashlight function; and a speaker 730 or audio transducer. In some embodiments the controller 170 further comprises I/O ports 735 for coupling to another device or computer system such a USB port, ports for battery recharging, and sensors 742, such as a microphone 739. The controller 170 may operate a single detainee's restraining device 110 or, alternatively, a controller may operate a selectable plurality of restraining devices 110.

This controller 170 may report and/or record status information such as remaining uses available on current power source 200 charge, time of use, duration of use, power source 200 availability, open or closed position of restraining device 110, physical location such as GPS coordinates, motion sensor readout, video signal playback, and audio sensor playback. The controller 170 may provide for stepped response activation. For instance, pressing an actuator to a first position may transit an activation signal to the restraining device 110 to initiate a warning such as vibration or audible warning on restraining device 110. Pressing the actuator to a second position (or alternatively, for a second time within a predetermined time period or a predefined plurality of presses) may cause the controller 170 to transmit an activation signal indicating that the restraining device 110 should initiate delivery of an electric shock of a predetermined first intensity and first predetermined duration. Pressing the actuator to a third position may cause the controller 170 to transmit an activation signal indicating that the restraining device 110 should initiate delivery of an additional electric shock of a second predetermined intensity and duration. In an alternate embodiment, pressing an actuator to a first position may enable recording of audio and/or video for a predetermined duration on and around restraining device 110, and the audio and/or video so recorded is stored in the memory 735 for later retrieval through the user interface or at least one I/O port 735. Among other advantages, automatic recording may assist correctional or law enforcement officers with a record of audible warnings issued prior to delivery of an electric shock. In another implementation, a usage log is stored in the memory 735, which comprises information regarding actuation of the restraining device 110 such as time and date of actuation, location of actuation, a unique identifier of the controller 170 and a unique identifier of the restraining device 110, identity of the detention official using the controller 170, confirmation of application of shock from restraining device 110, and the like.

The controller 170 of FIGS. 7A-7C may comprise any suitable form factor or size, and in one embodiment, is about the size of a conventional garage door opener. The controller 170 may be coupled to an individual through any suitable means such as through a holster, belt clip, strap, such as a wrist strap, integral to a piece of clothing such as on a vest or head covering. In the preferred embodiment a holster is utilized.

Security System

In some embodiments, the controller 170 may include an optional security system. This system may restrict unauthorized detainees from accessing, actuating, or disabling controller 170. For example, an authorized user may be required to enter a password in the user interface 725 to access functions within the device, and access will only be provided if the entered password matches a password previously stored within the controller. In another implementation, measurement of a biometric parameter such as an authorized user's voice or an authorized user's fingerprint is compared to an exemplar biometric measurement previously stored within the controller's memory 735, and access to the functions of the controller 170 is only provided if the measured biometric parameter matches the previously stored biometric parameter within a predetermined error range. Further, the security system 750 may comprise an authentication port for a mechanical tool such as a key, and will only allow the controller 170 to operate if a proper key is engaged in the authentication port. In an alternate embodiment, the security system 750 broadcasts a signal such as an RFID interrogation signal, and will only allow activation if a proper RFID interrogation response is received—in this way, detention officials wearing the proper RFID tag (such as integrated within a badge) would automatically be authorized to use the controller 170, but persons not having a proper RFID tag would be unable to use the device. Additionally, in some embodiments a safety is included so that the controller 170 is not inadvertently activated. This safety may be any suitable safety such as a toggle switch or button, a lever that must be moved from a first position to a second position, a slide at least partially covering the switch 710 and/or a warning command requesting a confirmation instruction. In another embodiment, an actuation signal will not be transmitted by the controller 170 unless a rapid succession of presses of the switch 710 occurs (such as three button presses within 1 second), preventing unintended actuation of the restraining device 110 by incidental contact with the actuator 710 of the controller 170. Alternatively, in one embodiment the electric shock component may not be activated until the restraining member 120 is in a second closed (locked) position, as detected by a switch within the sensors of the restraining device 110 coupled to the control system 160.

Restraint Involving A Plurality of Restraining Devices

A single restraining device 110 may be utilized in the system 100 or a plurality of restraining devices 110 may be attached to a detainee. For instance, a detainee may be fitted with restraining devices 110 around both wrists and/or both ankles. The restraining device 110 may be tethered to a fixed location physically or electronically. For instance, for electronic tethering, the control system 160 may be programmed so that a detainee may not travel further than a predetermined distance from a programmed location without activating the restraining device 110. Alternatively, restraining device 110 may be coupled to other restraints on the detainee or on other individuals or a fixed point, such as a coupler permanently fixed to floor, a seat on a vehicle, or an item of furniture such as a table. Though a pair of restraining devices 110 is proffered for restraint purposes, each restraining device 110 of a pair of restraining devices 110 may include a power source 200, and associated control system 160 for providing individual electric shock delivery. By having such independent control, redundancy is achieved and shocks may still be administered to a detainee should the detainee remove a body part from one restraining device 110 of a plurality of restraining devices 110 or open one restraining device 110 of a plurality of restraining devices from a closed position to an open position without authorization. In one embodiment the controller 170 has a default setting should one restraining device 110 of a plurality of restraining devices 110 not be available to provide an electric shock, a second restraining device of the plurality of restraining devices 110 will instead be activated to provide an electric shock response. Such alternative operation helps ensure that prompt activation of the unit and delivery of the electric shock is achieved.

Operation

Figure 8:
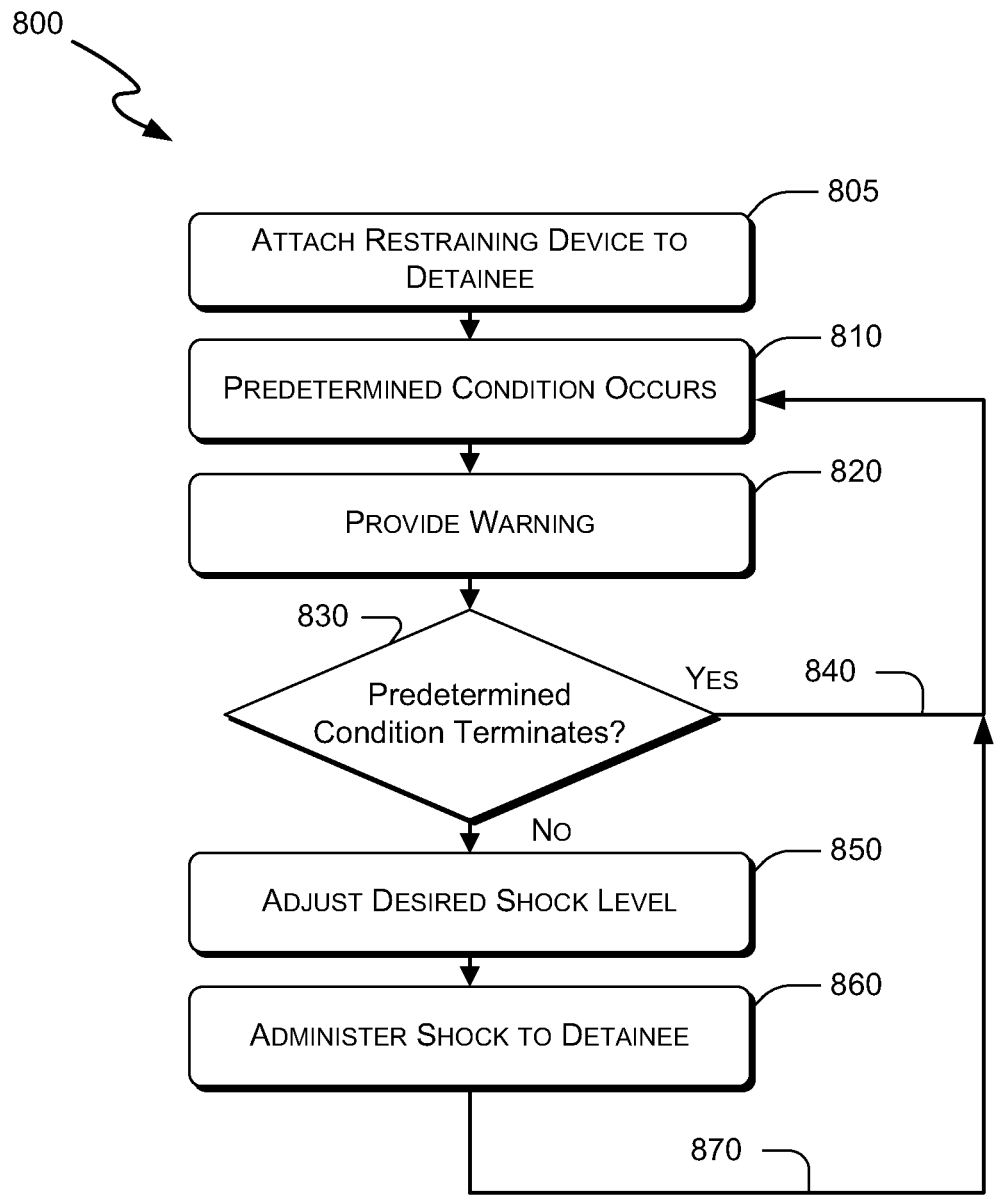
FIG. 8 depicts an operational flow chart of one embodiment of the present invention.

FIG. 8 shows a flow chart of one embodiment of a method of operation 800 of the present invention, and the method is presented in context of embodiments of devices of the present invention. In one embodiment, a restraining device is attached to a detainee 805, whereby a detainee places a portion of their body within an opening created by the receiving member and the restraining member while the receiving member and the restraining member are in an open position. The restraining member is then moved from an open position to a closed position that restrains at least a portion of a detainee's body. The closed position shall be selected from a plurality of closed positions to ensure a proper secure fit of the restraining member around the portion of a detainee's body. In one embodiment the electrodes/detainee interface 155 comprise smooth raised metal convex disks that approximate skin contact with the detainee. It is preferable that the electrodes 155 are in direct contact with the skin of the detainee, though the device will present an electric shock to the detainee through most clothing. The restraining devices facilitate restraining the movements of the affected body parts of the detainee. For instance, if the restraining devices are placed around the wrists of the detainee, the detainee will have limited use of their arms and hands and will not be able to forcibly break through a coupler that connects a pair of restraining devices together. Alternatively, if a single restraining device is placed over a wrist of the detainee and affixed to an external mounting point such as an eyelet securely attached to a wall, the detainee would be unable to move the arm to which the restraining device is attached in an unfettered manner.

A detainee may be placed in, or may place a portion of one or more body parts into restraining device 110. For instance, a prisoner may be a detainee and a prison guard may be an external controlling entity 1100 operating a controller 170, and the prison guard may wish to affix to the prisoner a pair of restraining devices 110 shown in FIG. 2 or FIG. 4A. The prison guard places both wrists of the prisoner into openings created between restraining members and the associated receiving members while the restraining device is in an open position. Then a prison guard moves the restraining members into locks on the receiving members creating a closed position to lock the restraining devices around the wrists of the prisoner. If the prisoner is also to have ankle restraints affixed, a prison guard may use another pair of restraining devices 110, placing both shins and/or ankles of a prisoner into openings created between other restraining members and the receiving members while the restraining devices are in an open position. Then a prison guard may move the restraining members into locks on their respective receiving members creating a closed position to lock the restraining devices around the shins and/or ankles of the prisoner. In an embodiment, all four restraining devices may be coupled together through a flexible chain, linkage, or cable. In one embodiment the prisoner would be capable of walking in a limited manner, such as shuffling, all while being restrained these by four restraining devices.

Returning to FIG. 8, once the restraining device is attached to the detainee, the process monitors for occurrence of a predetermined condition 810, which as described above may include a detention officer pressing a button, the detainee engaging in unauthorized behavior, or an external entity sending an actuation signal to the restraining device, or a computer program determining that a set of conditions has been violated or exceeded. In one implementation, the detainee to whom the restraining device is attached may be given a warning before any shock is administered, and if the predetermined condition ceases to occur 840, the process returns to monitoring and waiting for a predetermined condition to occur. The warning may be visual, such as a flashing light, sensory such as vibration, or audio such as a tone or command. If the warning is ignored and/or the actions that prompted the warning continue or additional inappropriate actions occur, a shock level may be adjusted 850 in one embodiment of the present invention, such as to a low initial level for a first shock, and a higher level for subsequent shocks. Alternatively, the output level of the shock to be administered is the same for all shocks. The shock is then administered to the detainee 860. If this first delivery of electric shock is ignored and/or the actions that prompted the first electric shock continue or additional inappropriate actions occur, the process may repeat, possibly with a warning followed by a second electric shock of a second intensity of a second duration for a second set number of pulses will be delivered to the detainee. The second intensity of electric shock may be the same voltage, less voltage or preferably greater voltage than the first intensity of electric shock. The second duration of electric shock may be the same duration, less duration or preferably greater duration than the first intensity of electric shock. The second set number of pulses of electric shock may be the same quantity, less quantity or preferably greater quantity than the first set number of pulses of electric shock. This stepped response may continue until the presets of the computer program and/or controller operator deem sufficient.

In various embodiments, safety mechanisms may be included in the control system 160 of the restraining device 110 and/or controller 170 to prevent a detainee from receiving greater than a predetermined nonlethal amount of electric shock in a predetermined period of time. In another embodiment, the detainee interface 155 receives electrical impulses from the detainee's heart, and returns them via EKG/EGG sensors to the sensor components 1107 for analysis by the control system 160. If the detainee's measured EKG is not measured to be in a safe range for administration of a shock (for instance, if fibrillation or arrhythmia is detected), the shock from the electric shock component 150 will be suppressed. In an alternate embodiment, if the measured EKG signal from the detainee interface 155 indicates a health issue, the control system 160 may send a message to an external entity 1100 through the communication interface 1007, indicating that the particular detainee is experiencing a health issue. In this manner, an external entity may avoid or suppress sending an activation signal to the restraining device, and/or summon medical care for the detainee.

Figure 7D:
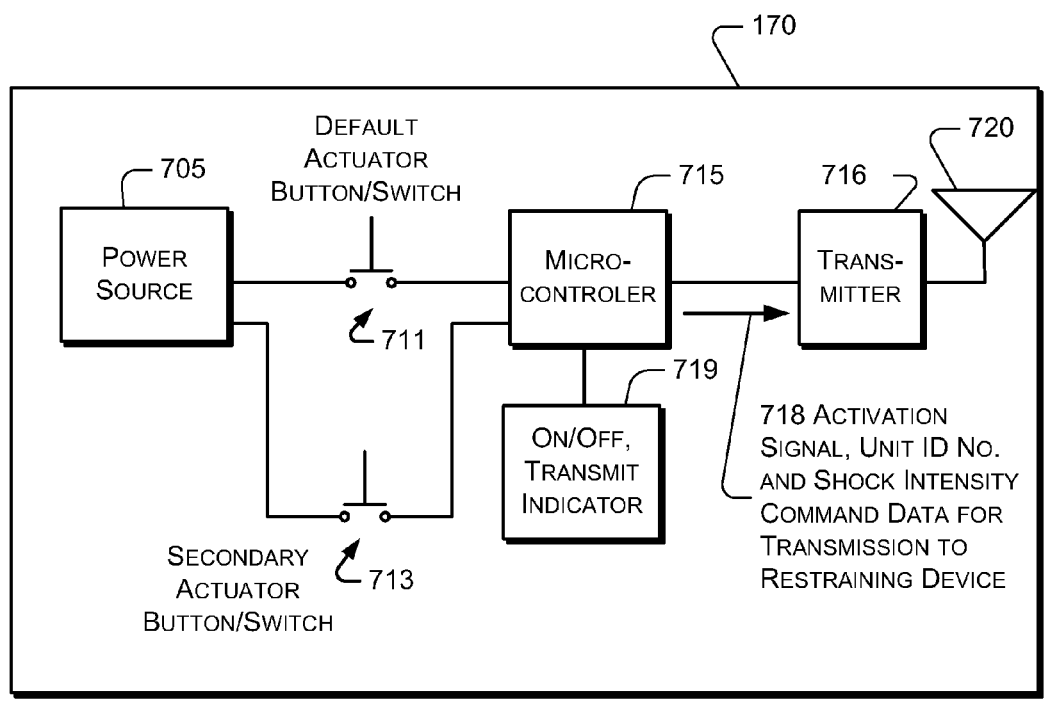
FIG. 7D depicts an alternative schematic block diagram of a controller of the current invention with two activation buttons/switches.

In another embodiment illustrated in FIG. 7D, a controller 170 of the present invention includes a user interface having a plurality of buttons, and the buttons may be disposed on the controller in any desired manner. For example, in one implementation, the controller comprises two buttons, a default shock delivery button, and a secondary shock delivery button, each respectively coupled to switches 711, 713 in the controller 170. The default shock delivery button may be disposed in a manner that is easier to depress than the secondary shock button; for example, the default shock button may be larger in size than the secondary shock button, the default shock button may be raised above a surface of the controller more than the secondary shock button, or the default shock button may resist depression with less spring force than the secondary shock button. The secondary shock button may also be disposed within a recess on the controller, making incidental actuation less likely than the default shock button.

When the default shock button is depressed, an actuation signal 718 is transmitted to the restraining device, causing the restraining device to administer a shock of a first intensity level and/or duration to the detainee, and if the secondary shock delivery button is depressed, an actuation signal is transmitted to the restraining device causing a shock of a second intensity level to be administered to the detainee. In one embodiment, the second shock intensity level causes more physiological distress to the detainee to whom the restraining device is attached than the first shock intensity level. In another embodiment, switches 711, 713 may be replaced by a rotary switch with a plurality of positions, each of which corresponds to a different level of shock to be administered to the detainee. For example, the rotary switch may comprise six positions, and a first position may cause an activation of the restraining device to administer a low level of shock, and each respective position of the rotary switch causes an shock of an increasing intensity and/or duration to be administered to the detainee, with position six corresponding to the highest permitted shock intensity and/or duration that may be administered to the detainee to whom the restraining device is attached.

The intensity and/or shock duration may be predetermined to provide any desired amount of physiological distress to a detainee to whom the restraining device is attached. In one embodiment, activating the restraining device (for example, by providing a single momentary button press of the default shock delivery button) causes the restraining device to administer a pulse train of eight current pulses of current at a 60 Hz rate with a single momentary button press. The eight pulse administration may be automatically repeated within a predetermined shock administration period, such as two pulse trains per second during a shock administration period while a shock administration button is being continuously depressed. A momentary actuation of a shock delivery button may cause a predetermined number of pulse trains to be generated, after which application of the shocks terminates unless the restraining device is again activated. As mentioned previously, the restraining device may include safety circuitry to limit or suppress administration of shocks below a predetermined threshold, such as limiting shocks to a maximum intensity and/or frequency within a predetermined shock window, and an optional predetermined reset/rest period (such as 10 seconds) that follows administration of a shock sequence before another shock may be administered to the detainee.

Any amount of current and/or voltage may be administered by the restraining device, to achieve restraint of the detainee. For example, given a 1.2 kΩ load (corresponding to an exemplary contact skin resistance of a detainee), up to 30 mA of current may be administered, and depending on the desired intensity selected by a person operating the controller, up to 32 volts potential may be applied to the electrodes of the restraining device delivering 27 mA of current to the detainee.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed:

1. A restraining device comprising: (a) a restraint for physically constraining movement of at least a portion of a detainee's body; (b) an electric shock component coupled to the restraint; (c) a control system coupled to the electric shock component, the control system configured to cause the electric shock component to deliver a shock to the detainee when a predetermined condition occurs; (d) a sensor in communication with the control system, wherein the sensor is configured to detect whether the detainee engages in an unauthorized activity; the control system is configured to deliver the shock to the detainee when the sensor indicates the detainee engages in the unauthorized activity.

2. The restraining device of claim 1, wherein the restraint includes at least one of: a handcuff; an ankle cuff; a restraining belt; a straightjacket; a harness; a facial restraint; a helmet; and a neck collar; and combinations thereof.

3. The restraining device of claim 1, wherein the restraint further includes one or more electrodes coupled to the electric shock component, wherein at least one of the one or more electrodes are configured to contact the skin of the detainee to deliver the shock.

4. The restraining device of claim 1, wherein the control system is configured to cause a warning to be provided to the detainee prior to delivering the shock.

5. The restraining device of claim 4, wherein the warning comprises one or more of: an audio warning; a tactile warning; a visual warning; and combinations thereof.

6. The restraining device of claim 5, wherein the control system is configured to vary an intensity of the warning.

7. The restraining device of claim 1, wherein the control system is configured to cause the electric shock component to vary at least one of: a magnitude of the electric shock; a frequency of a signal generating the electric shock; and a duration of the electric shock.

8. The restraining device of claim 1, wherein the unauthorized activity includes one or more of: entry into an unauthorized location; approaching a restricted area within a predetermined distance; approaching a keep-out zone broadcasting a keep-out signal, wherein a signal power level of the keep-out signal received by the device exceeds a predetermined threshold; exit from an authorized location; a threatening movement; an utterance by the detainee that exceeds a predetermined volume; an attempt to tamper with the restraining device; use of an unauthorized system; failure to provide a predetermined verbal acknowledgement; and combinations thereof.

9. The restraining device of claim 1, wherein the sensor is configured to measure and store one or more of: a status of the electric shock component; a status of the restraint; a status of the detainee; a record of shocks delivered or to the detainee.

10. The restraining device of claim 1, wherein the sensor includes one or more of: an accelerometer; an inclinometer; a potentiometer; a location sensing device; a microphone; a camera; a biometric sensor; and combinations thereof.

11. The restraining device of claim 1, wherein the control system is configured to communicate with one or more entities remote to the device, wherein the communication includes at least one of: a wireless data transmission; a transmission of an analog audio signal; a transmission of a signal digitally encoding at least one of audio information and data; a signal encoded with information comprising a command to be interpreted by the control system; a signal encoded with authentication information; and a signal comprising status information regarding the device.

12. The restraining device of claim 11, wherein communication between the control system and the one or more external entities includes one or more of: a command provided by the external entity to the control system, the command for controlling one or more functions of the device; a status provided by the control system to the external entity, the status relating to at least one of: data relating to the detainee; and one or more components of the device; a message provided by the external entity to the control system, the message for delivery to the detainee through one or more output devices in communication with the control system; information provided by the control system to the external entity, the information collected by one or more sensors in communication with the control system; and combinations thereof.

13. The restraining device of claim 11, wherein communication between the control system and the one or more external entities is encrypted.

14. The restraining device of claim 1, further comprising a substance delivery system in communication with the control system, wherein the control system is configured to cause the substance delivery system to expose the detainee to a substance.

15. The restraining device of claim 14, where the substance includes at least one of a liquid, a gas, a dye, an irritant, a medication, a sedative, a transdermal medication, a chemical restraint, a paralytic, a medication prescribed to the detainee, and combinations thereof.

* * * * *